United States Patent
Salzman et al.

(10) Patent No.: US 10,000,455 B2
(45) Date of Patent: *Jun. 19, 2018

(54) METHOD FOR TREATING DISEASES ASSOCIATED WITH OXIDATIVE STRESS OR ENDOTHELIAL DYSFUNCTION USING SUBSTITUTED 1-PYRROLIDINYLOXY, 1-PIPERIDINYLOXY AND 1-AZEPANYLOXY COMPOUNDS

(71) Applicant: SALZMAN GROUP, INC., West Tisbury, MA (US)

(72) Inventors: Andrew Lurie Salzman, West Tisbury, MA (US); Prakash Jagtap, North Andover, MA (US); Garry John Southan, Swampscott, MA (US)

(73) Assignee: Salzman Group, Inc., West Tisbury, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/470,739

(22) Filed: Mar. 27, 2017

(65) Prior Publication Data

US 2017/0327466 A1 Nov. 16, 2017

Related U.S. Application Data

(62) Division of application No. 14/769,078, filed as application No. PCT/IB2014/059451 on Mar. 5, 2014, now Pat. No. 9,604,932.

(60) Provisional application No. 61/772,861, filed on Mar. 5, 2013.

(51) Int. Cl.
- *C07D 207/46* (2006.01)
- *C07D 223/04* (2006.01)
- *C07D 211/94* (2006.01)

(52) U.S. Cl.
CPC ......... *C07D 223/04* (2013.01); *C07D 207/46* (2013.01); *C07D 211/94* (2013.01)

(58) Field of Classification Search
CPC .................................................... C07D 207/46
USPC ......................................................... 548/542
See application file for complete search history.

(56) References Cited

U.S. PATENT DOCUMENTS 6,455,542 B1   9/2002 Anggard et al.

FOREIGN PATENT DOCUMENTS

| WO | WO 1999037616 A1 | 7/1999 |
| WO | WO 2000030638 A1 | 6/2000 |
| WO | WO 2011/092690 | 8/2011 |
| WO | WO 2013/005216 | 1/2013 |
| WO | WO 2014/136059 | 9/2014 |

OTHER PUBLICATIONS

Kristiina M. Huttunen et al; "Prodrugs—from Serendipity to Rational Design" Pharmacological Reviews, vol. 63, No. 3. pp. 750-771. (2011).
Jarkko Rautio et al; "Prodrugs: design and clinical applications" Nature Reviews | Drug Discovery, vol. 7. pp. 255-270. (2008).
International Search Report and Written Opinion dated May 15, 2014 for PCT/IB2014/059451.
Jordan, V. C. Nature Reviews; Drug Discovery, 2, 2003, 205.
Vippagunta, et al. Advanced Drug Delivery Reviews, 48, 2001, 18.
Office Action received in Japanese Patent Application No. JP 2015-560829, dated Jan. 30, 2018.
Satoshi Syuto, Organic molecular pharmacology, 2nd edition, pp. 169-71.(2012).
Yordanov, Alexander T. et al., "Acyl-Protected Hydroxylamines as Spin Label Generators for EPR Brain Imaging" Journal of Medicinal Chemistry,45(11), pp. 2283-2288. (2002).

*Primary Examiner* — Douglas M Willis
(74) *Attorney, Agent, or Firm* — Knobbe, Martens, Olson & Bear, LLP

(57) ABSTRACT

A method reduces oxidative stress or endothelial dysfunction in a mammal. The method includes administering to the mammal a compound of formula I:

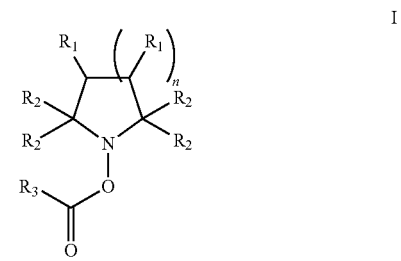

or an enantiomer, diastereomer, racemate, or a pharmaceutically acceptable salt of the compound.

20 Claims, 4 Drawing Sheets

METHOD FOR TREATING DISEASES ASSOCIATED WITH OXIDATIVE STRESS OR ENDOTHELIAL DYSFUNCTION USING SUBSTITUTED 1-PYRROLIDINYLOXY, 1-PIPERIDINYLOXY AND 1-AZEPANYLOXY COMPOUNDS

CROSS-REFERENCE TO RELATED APPLICATIONS

Any and all priority claims identified in the application data sheet, or any correction thereto, are hereby incorporated by reference under 37 C.F.R. 1.57 for example, this application is a divisional of and claims priority to U.S. application Ser. No. 14/769,078, filed Aug. 19, 2015 which is the U.S. National Phase of International Application No. PCT/IB2014/059451 filed Mar. 5, 2014, designating the U.S. and published as WO 2014/136059 on Sep. 12, 2014 which claims the benefit of U.S. Provisional Application No. 61/772,861 filed Mar. 5, 2013, each of which is incorporated herein by reference in its entirety.

TECHNICAL FIELD

The present invention provides prodrugs of compounds comprising a nitric oxide donor and a reactive oxygen species (ROS) degradation catalyst, and pharmaceutical compositions thereof.

BACKGROUND ART

U.S. Pat. Nos. 6,448,267, 6,455,542 and 6,759,430 disclose, inter alia, 1-pyrrolidinyloxy, 1-piperidinyloxy and 1-azepanyloxy derivatives comprising a nitric oxide donor and a $O_2^-$ scavenger, capable of acting as sources of nitric oxide and as ROS degradation catalysts, their preparation, and their use in the treatment of various conditions associated with oxidative stress or endothelial dysfunction such as diabetes mellitus and cardiovascular diseases.

International Publication No. WO 2012/093383 discloses methods and compositions for treatment of sepsis and conditions associated therewith using the compounds disclosed in U.S. Pat. Nos. 6,448,267, 6,455,542 and 6,759,430; International Publication No. WO 2011/092690 discloses methods and compositions for prevention, treatment, or management of pulmonary arterial hypertension (PAH) using those compounds; International Publication No. WO 2013/005216 discloses methods and compositions for prevention and treatment of renal ischemia-reperfusion injury; and International Publication No. WO 2013/190497 discloses methods and compositions for treatment of $Cl_2$ inhalational lung injury (CILI). The entire contents of each and all these patents and patent publications being herewith incorporated by reference in their entirety as if fully disclosed herein.

As shown in International Publication No. WO 2013/005216, the compounds disclosed in U.S. Pat. Nos. 6,448,267, 6,455,542 and 6,759,430, in particular 3-nitratomethyl-2,2,5,5-tetramethylpyrrolidinyloxy, herein identified R-100, that is specifically exemplified in the aforesaid International publications for treatment of sepsis, PAH, renal ischemia-reperfusion injury, and CILI, are highly insoluble in water but are soluble in certain organic solvents such as dimethyl sulfoxide (DMSO) or alternatively, when formulated as inclusion complexes with hydroxyalkylcyclodextrin such as hydroxypropylcyclodextrin (HPCD). The inclusion of such organic solvents in pharmaceutical compositions is potentially toxic and is thus preferably avoided. HPCD is relatively well tolerated but must be admixed with R-100 in a ratio of >20:1 (HPCD:R-100) in order to fully dissolve said compound. The upper limit of safety for clinical administration of HPCD is unknown, but the greatest amount approved for use in humans via an intravenous route is a daily quantity of 7 grams. Given the minimum usable ratio of 20:1 for the dissolution of R-100 and HPCD, and the limit of 7 grams of HPCD per day, the maximal amount of R-100 delivered in such an intravenous formulation would be 350 mg daily.

SUMMARY OF INVENTION

In order to overcome the limitations presented above, prodrugs of R-100, e.g., 2,2,5,5-tetramethyl-3-(nitrooxymethyl)pyrrolidin-1-yl acetate, herein identified R-107, have been prepared. As surprisingly found, R-107 is stable oil until exposure to plasma, after which it is readily converted to its corresponding 1-pyrrolidinyloxy derivative R-100. R-107 has a density of 1.12 mg/ml and may be administered in either pure form or diluted, e.g., in polyethyleneglycol (PEG)-400, via diverse routes including intravenous, intramuscular, subcutaneous, and topical, e.g., to the skin, wounds, ulcers, oral cavity, vagina, and anal canal.

In one aspect, the present invention thus provides a compound of the general formula I:

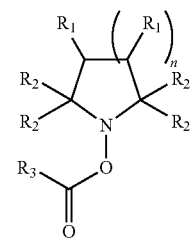

I or an enantiomer, diastereomer, racemate, or pharmaceutically acceptable salt or solvate thereof,
wherein
$R_1$ each independently is selected from H, —OH, —$COR_4$, —$COOR_4$, —$OCOOR_4$, —$OCON(R_4)_2$, —($C_1$-$C_{16}$)alkylene-$COOR_4$, —CN, —$NO_2$, —SH, —$SR_4$, —($C_1$-$C_{16}$)alkyl, —O—($C_1$-$C_{16}$)alkyl, —$N(R_4)_2$, —$CON(R_4)_2$, —$SO_2R_4$, —$SO_2NHR_4$, —S(=O)$R_4$, or a nitric oxide donor group of the formula —$X_1$—$X_2$—$X_3$, wherein $X_1$ is absent or selected from —O—, —S— or —NH—; $X_2$ is absent or is ($C_1$-$C_{20}$)alkylene optionally substituted by one or more —$ONO_2$ groups; and $X_3$ is —NO or —$ONO_2$, provided that at least one $R_1$ group is a nitric oxide donor group;
$R_2$ each independently is selected from ($C_1$-$C_{16}$)alkyl, ($C_2$-$C_{16}$)alkenyl, or ($C_2$-$C_{16}$)alkynyl;
$R_3$ is selected from ($C_1$-$C_{10}$)alkyl, ($C_3$-$C_{10}$)cycloalkyl, ($C_6$-$C_{14}$)aryl, or 4-12-membered heterocyclyl, each of which may optionally be substituted with —OH, —$COR_5$, —$COOR_5$, —($C_1$-$C_8$)alkylene-$COOR_5$, —CN, —$NO_2$, —($C_1$-$C_8$)alkyl, —O—($C_1$-$C_8$)alkyl, —$N(R_5)_2$, —CON$(R_5)_2$, —$SO_2R_5$, —$SO_2NHR_5$, or —S(=O)$R_5$;
$R_4$ each independently is selected from H, ($C_1$-$C_8$)alkyl, ($C_3$-$C_{10}$)cycloalkyl, ($C_6$-$C_{14}$)aryl, or 4-12-membered heterocyclyl, each of which other than H may optionally be substituted with —OH, —$COR_5$, —$COOR_5$, —$OCOOR_5$, —$OCON(R_5)_2$, —($C_1$-$C_8$)alkylene-$COOR_5$, —CN, —$NO_2$, —SH, —SR$_5$, —(C$_1$-C$_8$)alkyl, —O—(C$_1$-C$_8$)alkyl, —N(R$_5$)$_2$, —CON(R$_5$)$_2$, —SO$_2$R$_5$, —SO$_2$NHR$_5$, or —S(=O)R$_5$;

R$_5$ each independently is selected from H, (C$_1$-C$_8$)alkyl, (C$_3$-C$_{10}$)cycloalkyl, (C$_6$-C$_{14}$)aryl, or 4-12-membered heterocyclyl; and n is an integer of 1 to 3.

In another aspect, the present invention provides a pharmaceutical composition comprising a compound of the general formula I as defined above, or an enantiomer, diastereomer, racemate, or pharmaceutically acceptable salt or solvate thereof, and a pharmaceutically acceptable carrier. The compounds and pharmaceutical compositions of the present invention are useful for prevention, treatment or management of a disease, disorder or condition associated with oxidative stress or endothelial dysfunction.

In a further aspect, the present invention relates to a compound of the general formula I as defined above, or an enantiomer, diastereomer, racemate, or pharmaceutically acceptable salt or solvate thereof, for use in prevention, treatment or management of a disease, disorder or condition associated with oxidative stress or endothelial dysfunction.

In yet another aspect, the present invention relates to use of a compound of the general formula I as defined above, or an enantiomer, diastereomer, racemate, or pharmaceutically acceptable salt or solvate thereof, for the preparation of a pharmaceutical composition for prevention, treatment or management of a disease, disorder or condition associated with oxidative stress or endothelial dysfunction.

In still another aspect, the present invention relates to a method for prevention, treatment or management of a disease, disorder or condition associated with oxidative stress or endothelial dysfunction in an individual in need thereof, comprising administering to said individual an effective amount of a compound of the general formula I as defined above, or an enantiomer, diastereomer, racemate, or pharmaceutically acceptable salt or solvate thereof.

DETAILED DESCRIPTION OF THE INVENTION

Figure 1A:
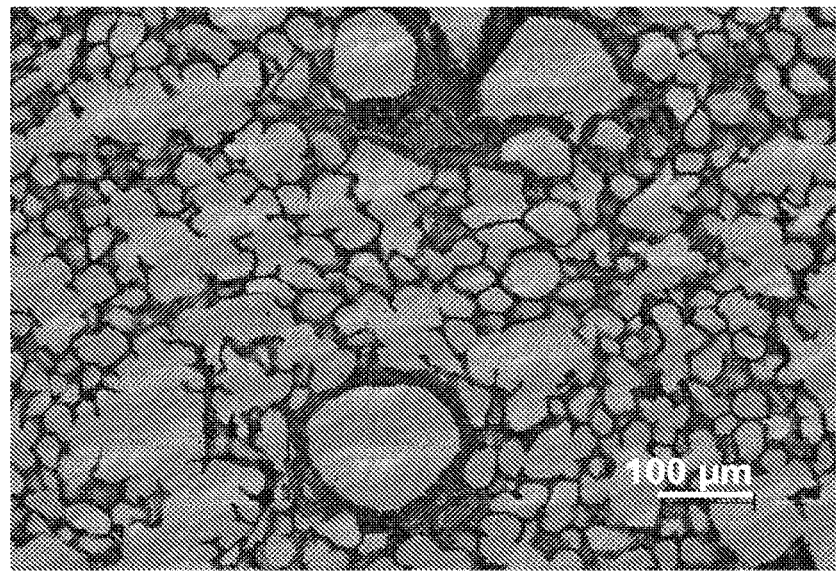
FIGS. 1A-1F show representative photomicrographs demonstrating hematoxylin/eosin-stained lung sections taken from sham-operated mice (1A, 1B); animals treated with Cl$_2$+HPCD (1C); animals treated with Cl$_2$+saline (1D); animals treated with Cl$_2$+R-100, 80 mg/kg/dose, IP (1E); and animals treated with Cl$_2$+R-107, 100 mg/kg/dose, IP (1F), as described in Example 16.
Figure 1B:
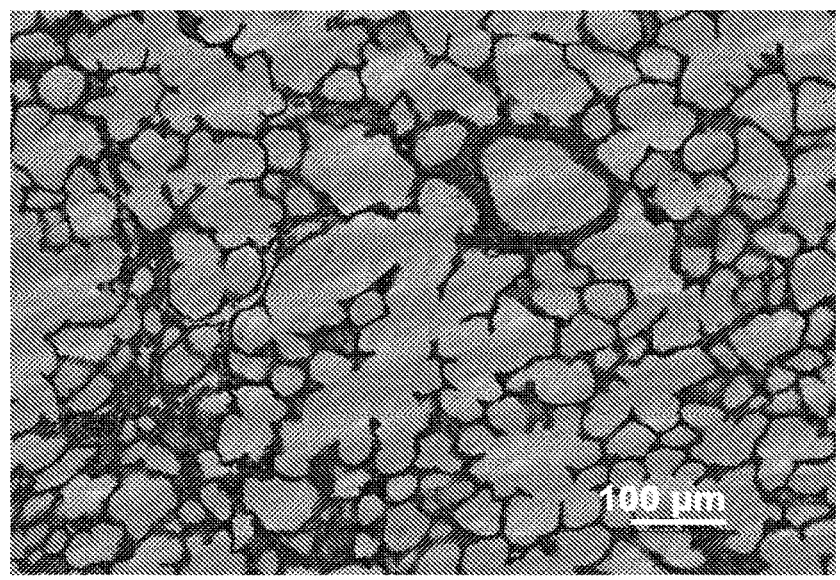
Figure 1C:
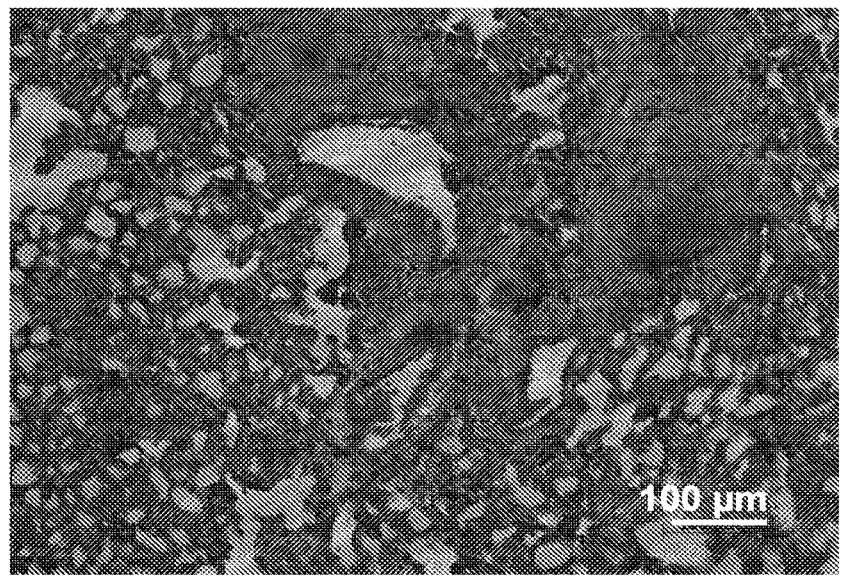
Figure 1D:
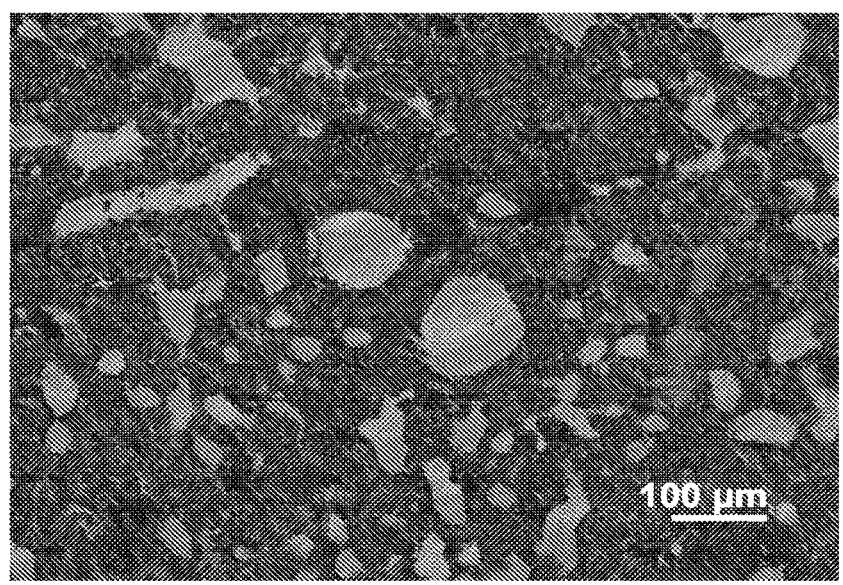
Figure 1E:
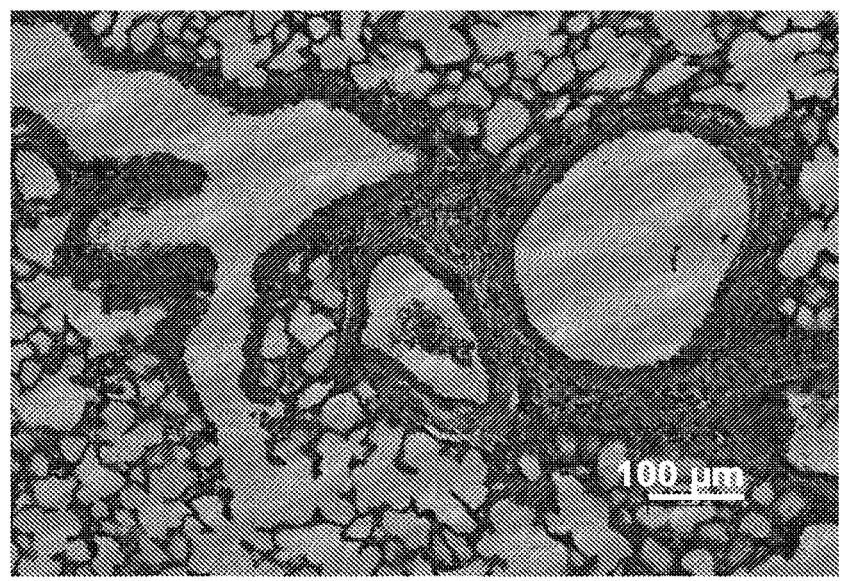
Figure 1F:
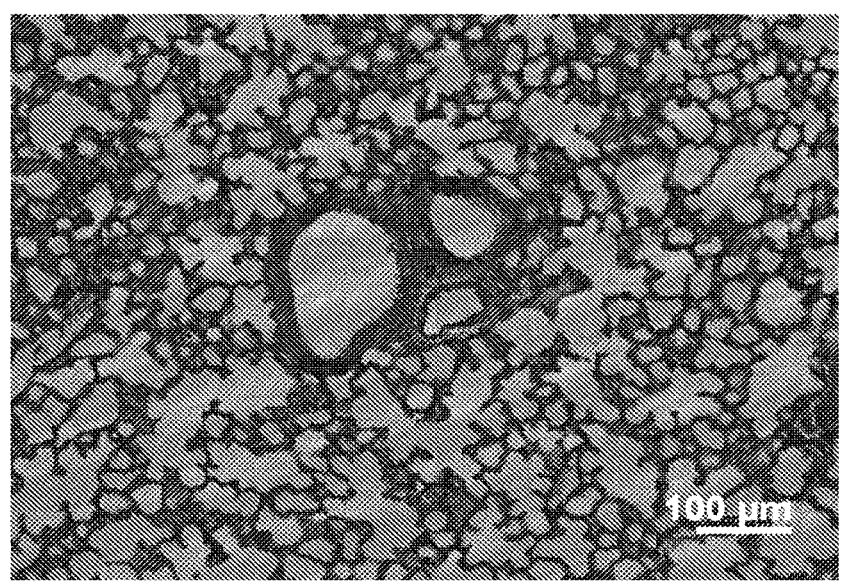

In one aspect, the present invention provides 1-pyrrolidinyl-, 1-piperidinyl- and 1-azepanyl-ester derivatives of the general formula I as defined above, comprising one to four nitric oxide donor groups and a ROS degradation catalyst, i.e., a superoxide anion (O$_2^-$) scavenger. The compounds of the present invention are, in fact, prodrugs for the corresponding hydroxylamine or N-hydroxyl (N—OH) compounds upon hydrolysis of the ester bond (O—C(O)R$_3$), and those hydroxylamine compounds are then oxidized, in vivo, to their corresponding nitroxide derivatives, more particularly 1-pyrrolidinyloxy, 1-piperidinyloxy, and 1-azepanyloxy derivatives disclosed in the aforesaid U.S. Pat. Nos. 6,448,267, 6,455,542 and 6,759,430. The compounds of the present invention are thus expected to be effective in all those clinical indications wherein the aforesaid 1-pyrrolidinyloxy, 1-piperidinyloxy, and 1-azepanyloxy derivatives are of benefit.

The term "alkyl" as used herein typically means a straight or branched saturated hydrocarbon radical having 1-16 carbon atoms and includes, e.g., methyl, ethyl, n-propyl, isopropyl, n-butyl, sec-butyl, isobutyl, tert-butyl, n-pentyl, isoamyl, 2,2-dimethylpropyl, n-hexyl, n-heptyl, n-octyl, n-nonyl, n-decyl, n-undecyl, n-dodecyl, n-tridecyl, n-tetradecyl, n-pentadecyl, n-hexadecyl, and the like. Preferred are (C$_1$-C$_8$)alkyl groups, more preferably (C$_1$-C$_4$)alkyl groups, most preferably methyl and ethyl. The terms "alkenyl" and "alkynyl" typically mean straight and branched hydrocarbon radicals having 2-16 carbon atoms and 1 double or triple bond, respectively, and include ethenyl, propenyl, 3-buten-1-yl, 2-ethenylbutyl, 3-octen-1-yl, 3-nonenyl, 3-decenyl, and the like, and propynyl, 2-butyn-1-yl, 3-pentyn-1-yl, 3-hexynyl, 3-octynyl, 4-decynyl, and the like. C$_2$-C$_6$ alkenyl and alkynyl radicals are preferred, more preferably C$_2$-C$_4$ alkenyl and alkynyl.

The term "alkylene" typically means a divalent straight or branched hydrocarbon radical having 1-20 carbon atoms and includes, e.g., methylene, ethylene, propylene, butylene, 2-methylpropylene, pentylene, 2-methylbutylene, hexylene, 2-methylpentylene, 3-methylpentylene, 2,3-dimethylbutylene, heptylene, octylene, and the like. Preferred are (C$_1$-C$_8$)alkylene, more preferably (C$_1$-C$_4$)alkylene, most preferably (C$_1$-C$_2$)alkylene.

The term "cycloalkyl" as used herein means a cyclic or bicyclic hydrocarbyl group having 3-10 carbon atoms such as cyclopropyl, cyclobutyl, cyclopentyl, cyclohexyl, cycloheptyl, cyclooctyl, adamantyl, bicyclo[3.2.1]octyl, bicyclo[2.2.1]heptyl, and the like. Preferred are (C$_5$-C$_{10}$)cycloalkyls, more preferably (C$_5$-C$_7$)cycloalkyls.

The term "aryl" denotes an aromatic carbocyclic group having 6-14 carbon atoms consisting of a single ring or multiple rings either condensed or linked by a covalent bond such as, but not limited to, phenyl, naphthyl, phenanthryl, and biphenyl.

The term "heterocyclic ring" denotes a mono- or polycyclic non-aromatic ring of 4-12 atoms containing at least one carbon atom and one to three heteroatoms selected from sulfur, oxygen or nitrogen, which may be saturated or unsaturated, i.e., containing at least one unsaturated bond. Preferred are 5- or 6-membered heterocyclic rings. The term "heterocyclyl" as used herein refers to any univalent radical derived from a heterocyclic ring as defined herein by removal of hydrogen from any ring atom. Examples of such radicals include, without limitation, piperidino, 4-morpholinyl, or pyrrolidinyl.

The term "nitric oxide donor group" as defined herein refers to any group of the formula —X$_1$—X$_2$—X$_3$, wherein X$_1$ may be absent or is selected from —O—, —S— or —NH—; X$_2$ may be absent or is (C$_1$-C$_{20}$)alkylene optionally substituted by one or more —ONO$_2$ groups; and X$_3$ is —NO or —ONO$_2$. Particular nitric oxide donor groups are those in which X$_1$ is absent or is —O—; X$_2$ is absent or is —(C$_1$-C$_6$)alkylene, preferably —(C$_1$-C$_3$)alkylene, more preferably methylene; X$_3$ is —NO or —ONO$_2$, preferably —ONO$_2$, and said alkylene is optionally substituted as defined hereinabove. According to the invention, the compound of the general formula I may comprise one nitric oxide donor group or more than one identical or different nitric oxide donor groups.

In certain embodiments, the compound of the present invention is a compound of the general formula I, wherein $R_1$ each independently is H, —COOR$_4$, —CON(R$_4$)$_2$, or a nitric oxide donor group; and $R_4$ is H.

In certain embodiments, the compound of the present invention is a compound of the general formula I, wherein $R_2$ each independently is ($C_1$-$C_8$)alkyl, preferably ($C_1$-$C_4$) alkyl, more preferably methyl or ethyl. In particular such embodiments, the $R_2$ groups are identical.

In certain embodiments, the compound of the present invention is a compound of the general formula I, wherein $R_3$ is ($C_1$-$C_8$)alkyl, preferably ($C_1$-$C_3$)alkyl, optionally substituted, preferably at a terminal carbon atom, with —OH, —N(R$_5$)$_2$, or —COOR$_5$, wherein $R_5$ each independently is ($C_1$-$C_8$)alkyl, preferably ($C_1$-$C_2$)alkyl, or H. In particular such embodiments, $R_3$ is ($C_1$-$C_8$)alkyl, preferably ($C_1$-$C_3$) alkyl, ($C_1$-$C_8$)alkylene-OH, preferably ($C_1$-$C_3$)alkylene-OH, ($C_1$-$C_8$)alkylene-N(R$_5$)$_2$, preferably ($C_1$-$C_3$)alkylene-N (R$_5$)$_2$, or ($C_1$-$C_8$)alkylene-COOR$_5$, preferably ($C_1$-$C_3$) alkylene-COOR$_5$.

In certain embodiments, the compound of the present invention is a compound of the general formula I, wherein in said nitric oxide donor group, $X_1$ is absent or —O—; $X_2$ is absent or ($C_1$-$C_{20}$)alkylene, preferably —($C_1$-$C_6$)alkylene, more preferably —($C_1$-$C_3$)alkylene, most preferably methylene; $X_3$ is —NO or —ONO$_2$, preferably —ONO$_2$; and said alkylene is optionally substituted by one or more —ONO$_2$ groups.

In certain embodiments, the compound of the present invention is a compound of the general formula I, wherein $R_1$ each independently is H, —COOR$_4$, —CON(R$_4$)$_2$, or a nitric oxide donor group; $R_2$ each independently is ($C_1$-$C_8$) alkyl, preferably ($C_1$-$C_4$)alkyl, more preferably methyl or ethyl; $R_3$ is ($C_1$-$C_8$)alkyl, preferably ($C_1$-$C_3$)alkyl, optionally substituted, preferably at a terminal carbon atom, with —OH, —N(R$_5$)$_2$, or —COOR$_5$; $R_4$ is H; $R_5$ each independently is ($C_1$-$C_8$)alkyl, preferably ($C_1$-$C_2$)alkyl, or H; and in said nitric oxide donor group, $X_1$ is absent or —O—; $X_2$ is absent or ($C_1$-$C_{20}$)alkylene, preferably —($C_1$-$C_6$)alkylene, more preferably —($C_1$-$C_3$)alkylene, most preferably methylene; $X_3$ is —NO or —ONO$_2$, preferably —ONO$_2$; and said alkylene is optionally substituted by one or more —ONO$_2$ groups.

In certain embodiments, the compound of the present invention is a compound of the general formula I, wherein $R_1$ to $R_5$ and the nitric oxide donor group(s) each independently is selected from the options defined by any one of the embodiments above; and n is 1, 2 or 3, i.e., a 1-pyrrolidinyl ester derivative of the formula Ia, 1-piperidinyl ester derivative of the formula Ib, or 1-azepanyl ester derivative of the formula Ic (see Table 1).

In certain particular embodiments, the compound of the present invention is a compound of the formula Ia in Table 1, wherein either the carbon atom at position 3 of the pyrrolidine ring or the carbon atom at position 4 of the pyrrolidine ring, or both, are each linked to a nitric oxide donor group. More particular such embodiments are those wherein each one of the nitric oxide donor groups independently is of the formula —($C_1$-$C_6$)alkylene-ONO$_2$, preferably —($C_1$-$C_3$)alkylene-ONO$_2$, more preferably —CH$_2$—ONO$_2$, or —O—($C_1$-$C_6$)alkylene-ONO$_2$, wherein said alkylene is optionally substituted by one or more —ONO$_2$ groups, or is —ONO$_2$.

In other particular embodiments, the compound of the present invention is a compound of the formula Ib in Table 1, wherein one, two or three of the carbon atoms at positions 3 to 5 of the piperidine ring are each linked to a nitric oxide donor group, i.e., (i) the carbon atom at position 3 of the piperidine ring and optionally one or more of the carbon atoms at positions 4 or 5 of the piperidine ring are each linked to a nitric oxide donor group; (ii) the carbon atom at position 4 of the piperidine ring and optionally one or more of the carbon atoms at positions 3 or 5 of the piperidine ring are each linked to a nitric oxide donor group; or (iii) the carbon atom at position 5 of the piperidine ring and optionally one or more of the carbon atoms at positions 3 or 4 of the piperidine ring are each linked to a nitric oxide donor group. More particular such embodiments are those wherein each one of the nitric oxide donor groups independently is of the formula —($C_1$-$C_6$)alkylene-ONO$_2$, preferably —($C_1$-$C_3$)alkylene-ONO$_2$, more preferably —CH$_2$—ONO$_2$, or —O—($C_1$-$C_6$)alkylene-ONO$_2$, wherein said alkylene is optionally substituted by one or more —ONO$_2$ groups, or is —ONO$_2$.

In further particular embodiments, the compound of the present invention is a compound of the formula Ic in Table 1, wherein one, two, three or four of the carbon atoms at positions 3 to 6 of the azepane ring are each linked to a nitric oxide donor group, i.e., (i) the carbon atom at position 3 of the azepane ring and optionally one or more of the carbon atoms at positions 4 to 6 of the azepane ring are each linked to a nitric oxide donor group; (ii) the carbon atom at position 4 of the azepane ring and optionally one or more of the carbon atoms at positions 3, 5 or 6 of the azepane ring are each linked to a nitric oxide donor group; (iii) the carbon atom at position 5 of the azepane ring and optionally one or more of the carbon atoms at positions 3, 4 or 6 of the azepane ring are each linked to a nitric oxide donor group; or (iv) the carbon atom at position 6 of the azepane ring and optionally one or more of the carbon atoms at positions 3 to 5 of the azepane ring are each linked to a nitric oxide donor group. More particular such embodiments are those wherein each one of the nitric oxide donor groups independently is of the formula —($C_1$-$C_6$)alkylene-ONO$_2$, preferably —($C_1$-$C_3$) alkylene-ONO$_2$, more preferably —CH$_2$—ONO$_2$, or —O— ($C_1$-$C_6$)alkylene-ONO$_2$, wherein said alkylene is optionally substituted by one or more —ONO$_2$ groups, or is —ONO$_2$.

TABLE 1

Structures Ia, Ib, and Ic, indicating 1-pyrrolidinyl-, 1-piperidinyl- and 1-azepanyl-ester derivatives, respectively

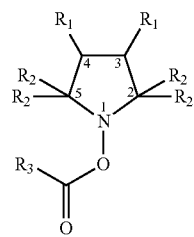

TABLE 1-continued

Structures Ia, Ib, and Ic, indicating 1-pyrrolidinyl-, 1-piperidinyl- and 1-azepanyl-ester derivatives, respectively

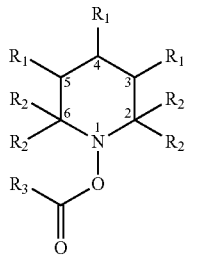

Ib

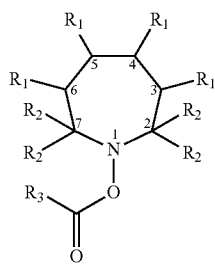

Ic

Specific compounds of the general formulas Ia, Ib, and Ic described herein, in which each one of the $R_1$ groups independently is either H or the nitric oxide donor group —$CH_2$—$ONO_2$, and $R_3$ is methyl, ethyl, or isopropyl, are herein identified compounds $1a_{1-3}$ to $15a_{1-3}$ in bold (compound $1a_1$ is also identified R-107), and their full chemical structures are depicted in Table 2. Similar compounds in which each one of the nitric oxide donor groups is —$ONO_2$ rather than —$CH_2$—$ONO_2$ are herein identified compounds $1b_{1-3}$ to $15b_{1-3}$ in bold. Other specific compounds of the general formulas Ia and Ib described herein, in which one $R_1$ group is the nitric oxide donor group —$CH_2$—$ONO_2$, another $R_1$ group is not H, and $R_3$ is methyl, ethyl, or isopropyl, are herein identified compounds $16a_{1-3}$ and $17a_{1-3}$ in bold, and their full chemical structures are depicted in Table 3. Similar compounds in which the nitric oxide donor group is —$ONO_2$ rather than —$CH_2$—$ONO_2$ are herein identified compounds $16b_{1-3}$ and $17b_{1-3}$ in bold. Further specific compounds of the general formula Ib described herein, in which one $R_1$ group is the nitric oxide donor group —O—$CH_2$—$CH(ONO_2)CH_2$—$ONO_2$, the other $R_1$ groups are H, and $R_3$ is methyl, ethyl, or isopropyl, are herein identified compounds $18_{1-3}$ in bold, and their full chemical structure is depicted in Table 3.

In specific embodiments, the compound of the invention is the compound of formula Ia, i.e., a compound of the general formula I in which n is 1, wherein $R_2$ each is methyl; $R_3$ is methyl, ethyl, or isopropyl; and (i) the $R_1$ group linked to the carbon atom at position 3 of the pyrrolidine ring is the nitric oxide donor group —$CH_2$—$ONO_2$; and the $R_1$ group linked to the carbon atom at position 4 of the pyrrolidine ring is H, i.e., 2,2,5,5-tetramethyl-3-(nitrooxymethyl)pyrrolidin-1-yl acetate, 2,2,5,5-tetramethyl-3-(nitrooxymethyl)pyrrolidin-1-yl propionate, and 2,2,5,5-tetramethyl-3-(nitrooxymethyl) pyrrolidin-1-yl isobutyrate (compounds $1a_1$, $1a_2$ and $1a_3$, respectively); (i) the $R_1$ group linked to the carbon atom at position 3 of the pyrrolidine ring is the nitric oxide donor group —$ONO_2$; and the $R_1$ group linked to the carbon atom at position 4 of the pyrrolidine ring is H, i.e., 2,2,5,5-tetramethyl-3-(nitrooxy)pyrrolidin-1-yl acetate, 2,2,5,5-tetramethyl-3-(nitrooxy) pyrrolidin-1-yl propionate, and 2,2,5,5-tetramethyl-3-(nitrooxy)pyrrolidin-1-yl isobutyrate (herein identified compounds $1b_1$, $1b_2$ and $1b_3$, respectively); (iii) each one of the $R_1$ groups linked to the carbon atoms at positions 3 and 4 of the pyrrolidine ring is the nitric oxide donor group —$CH_2$—$ONO_2$, i.e., 2,2,5,5-tetramethyl-3,4-bis(nitrooxymethyl) pyrrolidin-1-yl acetate, 2,2,5,5-tetramethyl-3,4-bis(nitrooxymethyl) pyrrolidin-1-yl propionate, and 2,2,5,5-tetramethyl-3,4-bis(nitrooxymethyl) pyrrolidin-1-yl isobutyrate (herein identified compounds $2a_1$, $2a_2$ and $2a_3$, respectively); or (iv) each one of the $R_1$ groups linked to the carbon atoms at positions 3 and 4 of the pyrrolidine ring is the nitric oxide donor group —$ONO_2$, i.e., 2,2,5,5-tetramethyl-3,4-bis(nitrooxy)pyrrolidin-1-yl acetate, 2,2,5,5-tetramethyl-3,4-bis(nitrooxy) pyrrolidin-1-yl propionate, and 2,2,5,5-tetramethyl-3,4-bis(nitrooxy)pyrrolidin-1-yl isobutyrate (herein identified compounds $2b_1$, $2b_2$ and $2b_3$, respectively).

In other specific embodiments, the compound of the invention is the compound of formula Ib, i.e., a compound of the general formula I wherein n is 2, wherein $R_2$ each is methyl; $R_3$ is methyl, ethyl, or isopropyl; and (i) the $R_1$ group linked to the carbon atom at position 3 of the piperidine ring is the nitric oxide donor group —$CH_2$—$ONO_2$; and each one of the $R_1$ groups linked to the carbon atoms at positions 4 and 5 of the piperidine ring is H, i.e., 2,2,6,6-tetramethyl-3-(nitrooxymethyl)piperidin-1-yl acetate, 2,2,6,6-tetramethyl-3-(nitrooxymethyl) piperidin-1-yl propionate, and 2,2,6,6-tetramethyl-3-(nitrooxymethyl) piperidin-1-yl isobutyrate (herein identified compounds $3a_1$, $3a_2$ and $3a_3$, respectively); (ii) the $R_1$ group linked to the carbon atom at position 3 of the piperidine ring is the nitric oxide donor group —$ONO_2$; and each one of the $R_1$ groups linked to the carbon atoms at positions 4 and 5 of the piperidine ring is H, i.e., 2,2,6,6-tetramethyl-3-(nitrooxy) piperidin-1-yl acetate, 2,2,6,6-tetramethyl-3-(nitrooxy)piperidin-1-yl propionate, and 2,2,6,6-tetramethyl-3-(nitrooxy) piperidin-1-yl isobutyrate (herein identified compounds $3b_1$, $3b_2$ and $3b_3$, respectively); (iii) the $R_1$ group linked to the carbon atom at position 4 of the piperidine ring is the nitric oxide donor group —$CH_2$—$ONO_2$; and each one of the $R_1$ groups linked to the carbon atoms at positions 3 and 5 of the piperidine ring is H, i.e., 2,2,6,6-tetramethyl-4-(nitrooxymethyl) piperidin-1-yl acetate, 2,2,6,6-tetramethyl-4-(nitrooxymethyl)piperidin-1-yl propionate, and 2,2,6,6-tetramethyl-4-(nitrooxymethyl) piperidin-1-yl isobutyrate (herein identified compounds $4a_1$, $4a_2$ and $4a_3$, respectively); (iv) the $R_1$ group linked to the carbon atom at position 4 of the piperidine ring is the nitric oxide donor group —$ONO_2$; and each one of the $R_1$ groups linked to the carbon atoms at positions 3 and 5 of the piperidine ring is H, i.e., 2,2,6,6-tetramethyl-4-(nitrooxy)piperidin-1-yl acetate, 2,2,6,6-tetramethyl-4-(nitrooxy)piperidin-1-yl propionate, and 2,2,6,6-tetramethyl-4-(nitrooxy)piperidin-1-yl isobutyrate (herein identified compounds $4b_1$, $4b_2$ and $4b_3$, respectively); (v) each one of the $R_1$ groups linked to the carbon atoms at positions 3 and 4 of the piperidine ring is the nitric oxide donor group —$CH_2$—$ONO_2$; and the $R_1$ group linked to the carbon atom at position 5 of the piperidine ring is H, i.e., 2,2,6,6-tetramethyl-3,4-bis(nitrooxymethyl)piperidin-1-yl acetate, 2,2,6,6-tetramethyl-3,4-bis(nitrooxymethyl)piperidin-1-yl propionate, and 2,2,6,6-tetramethyl-3,4-bis(nitrooxymethyl)piperidin-1-yl isobutyrate (herein identified compounds $5a_1$, $5a_2$ and $5a_3$, respectively); (vi) each one of the $R_1$ groups linked to the carbon atoms at positions 3 and 4 of the piperidine ring is the nitric oxide donor group —$ONO_2$; and the $R_1$ group linked to the carbon atom at position 5 of the piperidine ring is H, i.e., 2,2,6,6-tetramethyl-3,4-bis(nitrooxy)piperidin-1-yl acetate, 2,2,6,6-tetramethyl-3,4-bis(nitrooxy)piperidin-1-yl propionate, and 2,2,6,6-tetramethyl-3,4-bis(nitrooxy) piperidin-1-yl isobutyrate (herein identified compounds $5b_1$, $5b_2$ and $5b_3$, respectively); (vii) each one of the $R_1$ groups linked to the carbon atoms at positions 3 and 5 of the piperidine ring is the nitric oxide donor group —$CH_2$—$ONO_2$; and the $R_1$ group linked to the carbon atom at position 4 of the piperidine ring is H, i.e., 2,2,6,6-tetramethyl-3,5-bis(nitrooxymethyl)piperidin-1-yl acetate, 2,2,6,6-tetramethyl-3,5-bis(nitrooxymethyl)piperidin-1-yl propionate, and 2,2,6,6-tetramethyl-3,5-bis(nitrooxymethyl)piperidin-1-yl isobutyrate (herein identified compounds $6a_1$, $6a_2$ and $6a_3$, respectively); (viii) each one of the $R_1$ groups linked to the carbon atoms at positions 3 and 5 of the piperidine ring is the nitric oxide donor group —$ONO_2$; and the $R_1$ group linked to the carbon atom at position 4 of the piperidine ring is H, i.e., 2,2,6,6-tetramethyl-3,5-bis(nitrooxy)piperidin-1-yl acetate, 2,2,6,6-tetramethyl-3,5-bis(nitrooxy)piperidin-1-yl propionate, and 2,2,6,6-tetramethyl-3,5-bis(nitrooxy)piperidin-1-yl isobutyrate (herein identified compounds $6b_1$, $6b_2$ and $6b_3$, respectively); (ix) each one of the $R_1$ groups linked to the carbon atoms at positions 3 to 5 of the piperidine ring is the nitric oxide donor group —$CH_2$—$ONO_2$, i.e., 2,2,6,6-tetramethyl-3,4,5-tris(nitrooxymethyl) piperidin-1-yl acetate, 2,2,6,6-tetramethyl-3,4,5-tris(nitrooxymethyl) piperidin-1-yl propionate, and 2,2,6,6-tetramethyl-3,4,5-tris(nitrooxymethyl)piperidin-1-yl isobutyrate (herein identified compounds $7a_1$, $7a_2$ and $7a_3$, respectively); or (x) each one of the $R_1$ groups linked to the carbon atoms at positions 3 to 5 of the piperidine ring is the nitric oxide donor group —$ONO_2$, i.e., 2,2,6,6-tetramethyl-3,4,5-tris(nitrooxy) piperidin-1-yl acetate, 2,2,6,6-tetramethyl-3,4,5-tris(nitrooxy)piperidin-1-yl propionate, and 2,2,6,6-tetramethyl-3,4,5-tris(nitrooxy) piperidin-1-yl isobutyrate (herein identified compounds $7b_1$, $7b_2$ and $7b_3$, respectively).

In further specific embodiments, the compound used according to the method of the invention is the compound of formula Ic, i.e., a compound of the general formula I wherein n is 3, wherein $R_2$ each is methyl; $R_3$ is methyl, ethyl, or isopropyl; and (i) the $R_1$ group linked to the carbon atom at position 3 of the azepane ring is the nitric oxide donor group —$CH_2$—$ONO_2$; and each one of the $R_1$ groups linked to the carbon atoms at positions 4 to 6 of the azepane ring is H, i.e., 2,2,7,7-tetramethyl-3-(nitrooxymethyl)azepan-1-yl acetate, 2,2,7,7-tetramethyl-3-(nitrooxymethyl)azepan-1-yl propionate, and 2,2,7,7-tetramethyl-3-(nitrooxymethyl)azepan-1-yl isobutyrate (herein identified compounds $8a_1$, $8a_2$ and $8a_3$, respectively); (ii) the $R_1$ group linked to the carbon atom at position 3 of the azepane ring is the nitric oxide donor group —$ONO_2$; and each one of the $R_1$ groups linked to the carbon atoms at positions 4 to 6 of the azepane ring is H, i.e., 2,2,7,7-tetramethyl-3-(nitrooxy) azepan-1-yl acetate, 2,2,7,7-tetramethyl-3-(nitrooxy) azepan-1-yl propionate, and 2,2,7,7-tetramethyl-3-(nitrooxy) azepan-1-yl isobutyrate (herein identified compounds $8b_1$, $8b_2$ and $8b_3$, respectively); (iii) the $R_1$ group linked to the carbon atom at position 4 of the azepane ring is the nitric oxide donor group —$CH_2$—$ONO_2$; and each one of the $R_1$ groups linked to the carbon atoms at position 3, 5 and 6 of the azepane ring is H, i.e., 2,2,7,7-tetramethyl-4-(nitrooxymethyl)azepan-1-yl acetate, 2,2,7,7-tetramethyl-4-(nitrooxymethyl) azepan-1-yl propionate, and 2,2,7,7-tetramethyl-4-(nitrooxymethyl)azepan-1-yl isobutyrate (herein identified compounds $9a_1$, $9a_2$ and $9a_3$, respectively); (iv) the $R_1$ group linked to the carbon atom at position 4 of the azepane ring is the nitric oxide donor group —$ONO_2$; and each one of the $R_1$ groups linked to the carbon atoms at position 3, 5 and 6 of the azepane ring is H, i.e., 2,2,7,7-tetramethyl-4-(nitrooxy)azepan-1-yl acetate, 2,2,7,7-tetramethyl-4-(nitrooxy)azepan-1-yl propionate, and 2,2,7,7-tetramethyl-4-(nitrooxy) azepan-1-yl isobutyrate (herein identified compounds $9b_1$, $9b_2$ and $9b_3$, respectively); (v) each one of the $R_1$ groups linked to the carbon atoms at positions 3 and 4 of the azepane ring is the nitric oxide donor group —$CH_2$—$ONO_2$; and each one of the $R_1$ groups linked to the carbon atoms at positions 5 and 6 of the azepane ring is H, i.e., 2,2,7,7-tetramethyl-3,4-bis(nitrooxymethyl)azepan-1-yl acetate, 2,2,7,7-tetramethyl-3,4-bis(nitrooxymethyl) azepan-1-yl propionate, and 2,2,7,7-tetramethyl-3,4-bis(nitrooxymethyl)azepan-1-yl isobutyrate (herein identified compounds $10a_1$, $10a_2$ and $10a_3$, respectively); (vi) each one of the $R_1$ groups linked to the carbon atoms at positions 3 and 4 of the azepane ring is the nitric oxide donor group —$ONO_2$; and each one of the $R_1$ groups linked to the carbon atoms at positions 5 and 6 of the azepane ring is H, i.e., 2,2,7,7-tetramethyl-3,4-bis(nitrooxy)azepan-1-yl acetate, 2,2,7,7-tetramethyl-3,4-bis(nitrooxy)azepan-1-yl propionate, and 2,2,7,7-tetramethyl-3,4-bis(nitrooxy) azepan-1-yl isobutyrate (herein identified compounds $10b_1$, $10b_2$ and $10b_3$, respectively); (vii) each one of the $R_1$ groups linked to the carbon atoms at positions 3 and 5 of the azepane ring is the nitric oxide donor group —$CH_2$—$ONO_2$; and each one of the $R_1$ groups linked to the carbon atoms at positions 4 and 6 of the azepane ring is H, i.e., 2,2,7,7-tetramethyl-3,5-bis(nitrooxymethyl)azepan-1-yl acetate, 2,2,7,7-tetramethyl-3,5-bis(nitrooxymethyl)azepan-1-yl propionate, and 2,2,7,7-tetramethyl-3,5-bis(nitrooxymethyl) azepan-1-yl isobutyrate (herein identified compounds $11a_1$, $11a_2$ and $11a_3$, respectively); (viii) each one of the $R_1$ groups linked to the carbon atoms at positions 3 and 5 of the azepane ring is the nitric oxide donor group —$ONO_2$; and each one of the $R_1$ groups linked to the carbon atoms at positions 4 and 6 of the azepane ring is H, i.e., 2,2,7,7-tetramethyl-3,5-bis(nitrooxy)azepan-1-yl acetate, 2,2,7,7-tetramethyl-3,5-bis(nitrooxy) azepan-1-yl propionate, and 2,2,7,7-tetramethyl-3,5-bis(nitrooxy)azepan-1-yl isobutyrate (herein identified compounds $11b_1$, $11b_2$ and $11b_3$, respectively); (ix) each one of the $R_1$ groups linked to the carbon atoms at positions 3 and 6 of the azepane ring is the nitric oxide donor group —$CH_2$—$ONO_2$; and each one of the $R_1$ groups linked to the carbon atoms at positions 4 and 5 of the azepane ring is H, i.e., 2,2,7,7-tetramethyl-3,6-bis(nitrooxymethyl)azepan-1-yl acetate, 2,2,7,7-tetramethyl-3,6-bis(nitrooxymethyl)azepan-1-yl propionate, and 2,2,7,7-tetramethyl-3,6-bis(nitrooxymethyl)azepan-1-yl isobutyrate (herein identified compounds $12a_1$, $12a_2$ and $12a_3$, respectively); (x) each one of the $R_1$ groups linked to the carbon atoms at positions 3 and 6 of the azepane ring is the nitric oxide donor group —$ONO_2$; and each one of the $R_1$ groups linked to the carbon atoms at positions 4 and 5 of the azepane ring is H, i.e., 2,2,7,7-tetramethyl-3,6-bis(nitrooxy) azepan-1-yl acetate, 2,2,7,7-tetramethyl-3,6-bis(nitrooxy) azepan-1-yl propionate, and 2,2,7,7-tetramethyl-3,6-bis(nitrooxy)azepan-1-yl isobutyrate (herein identified compounds $12b_1$, $12b_2$ and $12b_3$, respectively); (xi) each one of the $R_1$ groups linked to the carbon atoms at positions 3 to 5 of the azepane ring is the nitric oxide donor group —$CH_2$—$ONO_2$; and the $R_1$ group linked to the carbon atom at position 6 of the azepane ring is H, i.e., 2,2,7,7-tetramethyl-3,4,5-tris(nitrooxymethyl) azepan-1-yl acetate, 2,2,7,7-tetramethyl-3,4,5-tris(nitrooxymethyl) azepan-1-yl propionate, and 2,2,7,7-tetramethyl-3,4,5-tris(nitrooxymethyl) azepan-1-yl isobutyrate (herein identified compounds $13a_1$, 13a$_2$ and 13a$_3$, respectively); (xii) each one of the R$_1$ groups linked to the carbon atoms at positions 3 to 5 of the azepane ring is the nitric oxide donor group —ONO$_2$; and the R$_1$ group linked to the carbon atom at position 6 of the azepane ring is H, i.e., 2,2,7,7-tetramethyl-3,4,5-tris(nitrooxy)azepan-1-yl acetate, 2,2,7,7-tetramethyl-3,4,5-tris(nitrooxy) azepan-1-yl propionate, and 2,2,7,7-tetramethyl-3,4,5-tris (nitrooxy) azepan-1-yl isobutyrate (herein identified compounds 13b$_1$, 13b$_2$ and 13b$_3$, respectively); (xiii) each of the R$_1$ groups linked to the carbon atoms at positions 3, 4 and 6 of the azepane ring is the nitric oxide donor group —CH$_2$—ONO$_2$; and the R$_1$ group linked to the carbon atom at position 5 of the azepane ring is H, i.e., 2,2,7,7-tetramethyl-3,4,6-tris(nitrooxymethyl)azepan-1-yl acetate, 2,2,7,7-tetramethyl-3,4,6-tris(nitrooxymethyl) azepan-1-yl propionate, and 2,2,7,7-tetramethyl-3,4,6-tris(nitrooxymethyl) azepan-1-yl isobutyrate (herein identified compounds 14a$_1$, 14a$_2$ and 14a$_3$, respectively); (xiv) each of the R$_1$ groups linked to the carbon atoms at positions 3, 4 and 6 of the azepane ring is the nitric oxide donor group —ONO$_2$; and the R$_1$ group linked to the carbon atom at position 5 of the azepane ring is H, i.e., 2,2,7,7-tetramethyl-3,4,6-tris(nitrooxy) azepan-1-yl acetate, 2,2,7,7-tetramethyl-3,4,6-tris (nitrooxy)azepan-1-yl propionate, and 2,2,7,7-tetramethyl-3,4,6-tris(nitrooxy)azepan-1-yl isobutyrate (herein identified compounds 14b$_1$, 14b$_2$ and 14b$_3$, respectively); (xv) each of the R$_1$ groups linked to the carbon atoms at positions 3 to 6 of the azepane ring is the nitric oxide donor group —CH$_2$—ONO$_2$, i.e., 2,2,7,7-tetramethyl-3,4,5,6-tetrakis(nitrooxymethyl) azepan-1-yl acetate, 2,2,7,7-tetramethyl-3,4,5,6-tetrakis (nitrooxymethyl)azepan-1-yl propionate, and 2,2,7,7-tetramethyl-3,4,5,6-tetrakis (nitrooxymethyl)azepan-1-yl isobutyrate (herein identified compounds 15a$_1$, 15a$_2$ and 15a$_3$, respectively); or (xvi) each of the R$_1$ groups linked to the carbon atoms at positions 3 to 6 of the azepane ring is the nitric oxide donor group —ONO$_2$, i.e., 2,2,7,7-tetramethyl-3,4,5,6-tetrakis(nitrooxy) azepan-1-yl acetate, 2,2,7,7-tetramethyl-3,4,5,6-tetrakis(nitrooxy) azepan-1-yl propionate, and 2,2,7,7-tetramethyl-3,4,5,6-tetrakis (nitrooxy)azepan-1-yl isobutyrate (herein identified compounds 15b$_1$, 15b$_2$ and 15b$_3$, respectively).

In still other specific embodiments, the compound of the invention is the compound of formula Ia, wherein R$_2$ each is methyl; R$_3$ is methyl, ethyl, or isopropyl; and (i) the R$_1$ group linked to the carbon atom at position 3 of the pyrrolidine ring is the nitric oxide donor group —CH$_2$—ONO$_2$; and the R$_1$ group linked to the carbon atom at position 4 of the pyrrolidine ring is —CONH$_2$, i.e., 2,2,5,5-tetramethyl-3-(nitrooxymethyl)-4-carbamoyl-pyrrolidin-1-yl acetate, 2,2,5,5-tetramethyl-3-(nitrooxymethyl)-4-carbamoyl-pyrrolidin-1-yl propionate, and 2,2,5,5-tetramethyl-3-(nitrooxymethyl)-4-carbamoyl-pyrrolidin-1-yl isobutyrate (herein identified compounds 16a$_1$, 16a$_2$ and 16a$_3$, respectively); or (ii) the R$_1$ group linked to the carbon atom at position 3 of the pyrrolidine ring is the nitric oxide donor group —ONO$_2$; and the R$_1$ group linked to the carbon atom at position 4 of the pyrrolidine ring is —CONH$_2$, i.e., 2,2,5,5-tetramethyl-3-(nitrooxy)-4-carbamoyl-pyrrolidin-1-yl acetate, 2,2,5,5-tetramethyl-3-(nitrooxy)-4-carbamoyl-pyrrolidin-1-yl propionate, and 2,2,5,5-tetramethyl-3-(nitrooxy)-4-carbamoyl-pyrrolidin-1-yl isobutyrate (herein identified compounds 16b$_1$, 16b$_2$ and 16b$_3$, respectively).

In yet other specific embodiments, the compound of the invention is the compound of formula Ib, wherein R$_2$ each is methyl; R$_3$ is methyl, ethyl, or isopropyl; and (i) the R$_1$ group linked to the carbon atom at position 3 of the piperidine ring is the nitric oxide donor group —CH$_2$—ONO$_2$; the R$_1$ group linked to the carbon atom at position 4 of the piperidine ring is —COOH; and the R$_1$ group linked to the carbon atoms at position 5 of the piperidine ring is H, i.e., 2,2,6,6-tetramethyl-3-(nitrooxymethyl)-4-carboxy-piperidin-1-yl acetate, 2,2,6,6-tetramethyl-3-(nitrooxymethyl)-4-carboxy-piperidin-1-yl propionate, and 2,2,6,6-tetramethyl-3-(nitrooxymethyl)-4-carboxy-piperidin-1-yl isobutyrate (herein identified compounds 17a$_1$, 17a$_2$ and 17a$_3$, respectively); or (ii) the R$_1$ group linked to the carbon atom at position 3 of the piperidine ring is the nitric oxide donor group —ONO$_2$; the R$_1$ group linked to the carbon atom at position 4 of the piperidine ring is —COOH; and the R$_1$ group linked to the carbon atoms at position 5 of the piperidine ring is H, i.e., 2,2,6,6-tetramethyl-3-(nitrooxy)-4-carboxy-piperidin-1-yl acetate, 2,2,6,6-tetramethyl-3-(nitrooxy)-4-carboxy-piperidin-1-yl propionate, and 2,2,6,6-tetramethyl-3-(nitrooxy)-4-carboxy-piperidin-1-yl isobutyrate (herein identified compounds 17b$_1$, 17b$_2$ and 17b$_3$, respectively).

TABLE 2

Compounds of the general formula I, herein identified 1a$_{1-3}$ to 15a$_{1-3}$*

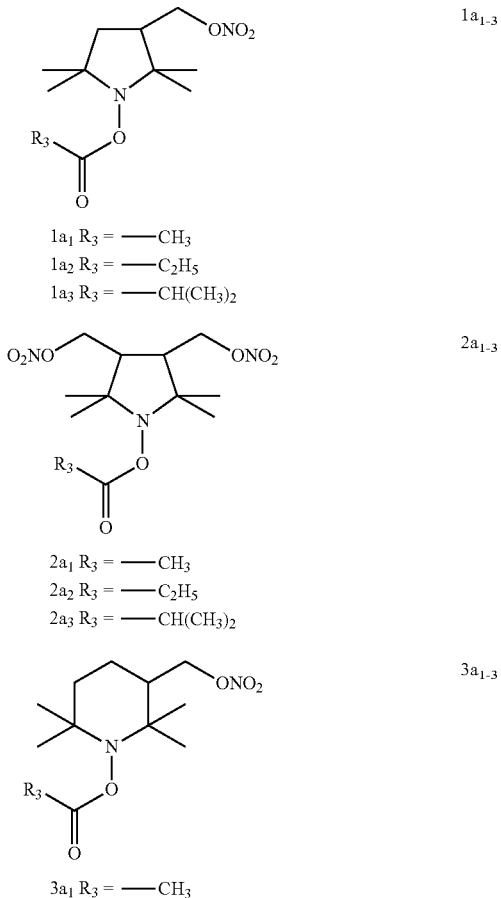

TABLE 2-continued

Compounds of the general formula I, herein identified $1a_{1-3}$ to $15a_{1-3}$*

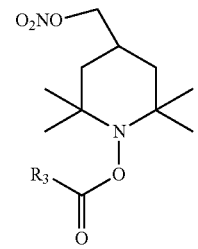

$4a_{1-3}$ $4a_1$ $R_3 = $ —CH$_3$
$4a_2$ $R_3 = $ —C$_2$H$_5$
$4a_3$ $R_3 = $ —CH(CH$_3$)$_2$

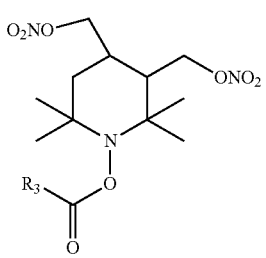

$5a_{1-3}$ $5a_1$ $R_3 = $ —CH$_3$
$5a_2$ $R_3 = $ —C$_2$H$_5$
$5a_3$ $R_3 = $ —CH(CH$_3$)$_2$

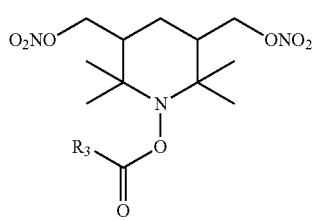

$6a_{1-3}$ $6a_1$ $R_3 = $ —CH$_3$
$6a_2$ $R_3 = $ —C$_2$H$_5$
$6a_3$ $R_3 = $ —CH(CH$_3$)$_2$

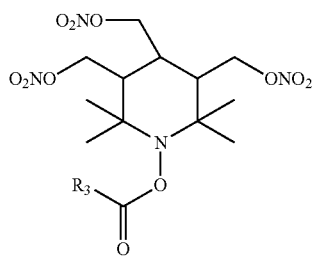

$7a_{1-3}$ $7a_1$ $R_3 = $ —CH$_3$
$7a_2$ $R_3 = $ —C$_2$H$_5$
$7a_3$ $R_3 = $ —CH(CH$_3$)$_2$

TABLE 2-continued

Compounds of the general formula I, herein identified $1a_{1-3}$ to $15a_{1-3}$*

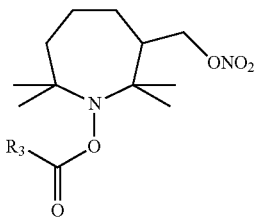

$8a_{1-3}$ $8a_1$ $R_3 = $ —CH$_3$
$8a_2$ $R_3 = $ —C$_2$H$_5$
$8a_3$ $R_3 = $ —CH(CH$_3$)$_2$

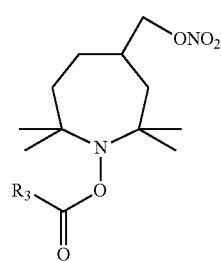

$9a_{1-3}$ $9a_1$ $R_3 = $ —CH$_3$
$9a_2$ $R_3 = $ —C$_2$H$_5$
$9a_3$ $R_3 = $ —CH(CH$_3$)$_2$

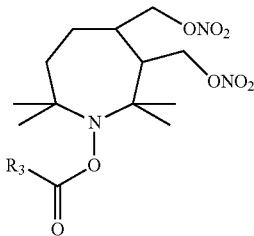

$10a_{1-3}$ $10a_1$ $R_3 = $ —CH$_3$
$10a_2$ $R_3 = $ —C$_2$H$_5$
$10a_3$ $R_3 = $ —CH(CH$_3$)$_2$

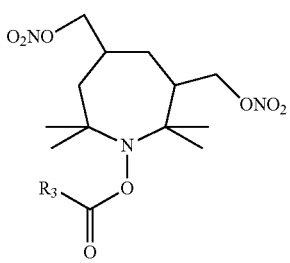

$11a_{1-3}$ $11a_1$ $R_3 = $ —CH$_3$
$11a_2$ $R_3 = $ —C$_2$H$_5$
$11a_3$ $R_3 = $ —CH(CH$_3$)$_2$

TABLE 2-continued

Compounds of the general formula I, herein identified $1a_{1-3}$ to $15a_{1-3}$*

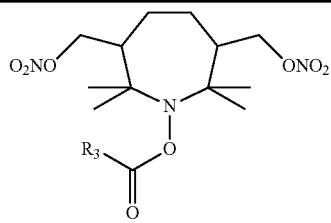

$12a_{1-3}$ $12a_1$ $R_3 =$ —$CH_3$
$12a_2$ $R_3 =$ —$C_2H_5$
$12a_3$ $R_3 =$ —$CH(CH_3)_2$

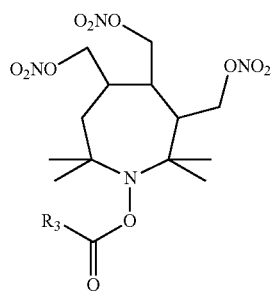

$13a_{1-3}$ $13a_1$ $R_3 =$ —$CH_3$
$13a_2$ $R_3 =$ —$C_2H_5$
$13a_3$ $R_3 =$ —$CH(CH_3)_2$

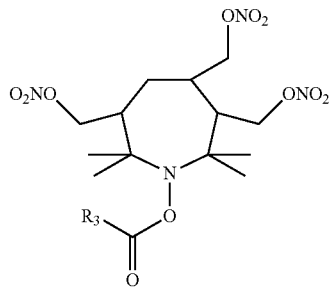

$14a_{1-3}$ $14a_1$ $R_3 =$ —$CH_3$
$14a_2$ $R_3 =$ —$C_2H_5$
$14a_3$ $R_3 =$ —$CH(CH_3)_2$

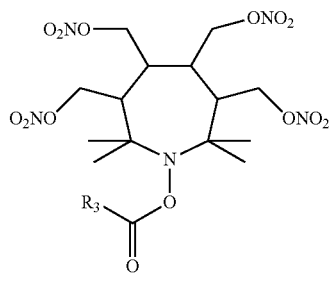

$15a_{1-3}$ $15a_1$ $R_3 =$ —$CH_3$
$15a_2$ $R_3 =$ —$C_2H_5$
$15a_3$ $R_3 =$ —$CH(CH_3)_2$

*Similar compounds in which each one of the nitric oxide donor groups is —$ONO_2$ rather than —$CH_2$—$ONO_2$ are herein identified compounds $1b_{1-3}$ to $15b_{1-3}$ In still a further specific embodiment, the compound of the invention is the compound of formula Ib, wherein $R_2$ each is methyl; $R_3$ is methyl, ethyl, or isopropyl; the $R_1$ group linked to the carbon atom at position 4 of the piperidine ring is the nitric oxide donor group —O—$CH_2$—$CH(ONO_2)CH_2$—$ONO_2$; and each of the $R_1$ groups linked to the carbon atoms at positions 3 and 5 of the piperidine ring is H, i.e., 2,2,6,6-tetramethyl-4-(2,3-bis(nitrooxy)propyloxy)-piperidin-1-yl acetate, 2,2,6,6-tetramethyl-4-(2,3-bis(nitrooxy)propyloxy)-piperidin-1-yl propionate, and 2,2,6,6-tetramethyl-4-(2,3-bis(nitrooxy)propyloxy)-piperidin-1-yl isobutyrate (herein identified compounds $18_1$, $18_2$ and $18_3$, respectively).

The compounds of the present invention may be synthesized according to any technology or procedure known in the art, e.g., as described with respect to compounds $1a_1$, $1a_2$ and $1a_3$ in the Examples section hereinafter.

TABLE 3

Compounds of the formula I, herein identified $16a_{1-3}$*, $17a_{1-3}$* and $18_{1-3}$

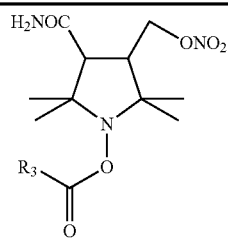

$16a_{1-3}$ $16a_1$ $R_3 =$ —$CH_3$
$16a_2$ $R_3 =$ —$C_2H_5$
$16a_3$ $R_3 =$ —$CH(CH_3)_2$

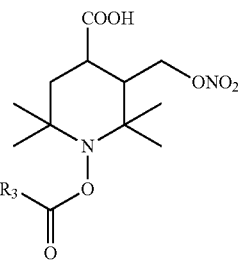

$17a_{1-3}$ $17a_1$ $R_3 =$ —$CH_3$
$17a_2$ $R_3 =$ —$C_2H_5$
$17a_3$ $R_3 =$ —$CH(CH_3)_2$

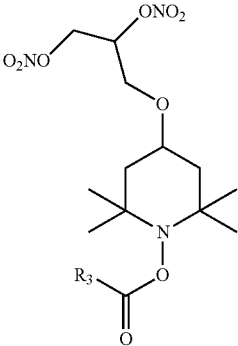

$18_{1-3}$ $18_1$ $R_3 =$ —$CH_3$
$18_2$ $R_3 =$ —$C_2H_5$
$18_3$ $R_3 =$ —$CH(CH_3)_2$

*Similar compounds in which each one of the nitric oxide donor group is —$ONO_2$ rather than —$CH_2$—$ONO_2$ are herein identified compounds $16b_{1-3}$ and $17b_{1-3}$ The compounds of the general formula I may have one or more asymmetric centers, and may accordingly exist both as enantiomers, i.e., optical isomers (R, S, or racemate, wherein a certain enantiomer may have an optical purity of 90%, 95%, 99% or more) and as diastereoisomers. Specifically, those chiral centers may be, e.g., in each one of the carbon atoms of the 1-pyrrolidinyl ester derivative, 1-piperidinyl ester derivative; and 1-azepanyl ester derivative of the general formulas Ia, Ib and Ic, respectively. It should be understood that the present invention encompasses all such enantiomers, isomers and mixtures thereof, as well as pharmaceutically acceptable salts and solvates thereof.

Optically active forms of the compounds of the general formula I may be prepared using any method known in the art, e.g., by resolution of the racemic form by recrystallization techniques; by chiral synthesis; by extraction with chiral solvents; or by chromatographic separation using a chiral stationary phase. A non-limiting example of a method for obtaining optically active materials is transport across chiral membranes, i.e., a technique whereby a racemate is placed in contact with a thin membrane barrier, the concentration or pressure differential causes preferential transport across the membrane barrier, and separation occurs as a result of the non-racemic chiral nature of the membrane that allows only one enantiomer of the racemate to pass through. Chiral chromatography, including simulated moving bed chromatography, can also be used. A wide variety of chiral stationary phases are commercially available.

The compounds of the present invention are prodrugs of the corresponding 1-pyrrolidinyloxy, 1-piperidinyloxy, and 1-azepanyloxy derivatives disclosed in U.S. Pat. Nos. 6,448,267, 6,455,542 and 6,759,430, and are thus expected to be effective in all those clinical indications wherein those compounds are of benefit, i.e., in the prevention, treatment or management of any condition associated with oxidative stress or endothelial dysfunction. Such conditions include, without being limited to, retinal ischemia reperfusion injury; acute anterior ischemic optic neuropathy; central retinal artery occlusion; hemolytic diseases, including spherocytosis, G6PD deficiency, sickle cell disease, thalassemias, and paroxysmal nocturnal hemoglobinuria; diabetes mellitus, including diabetic wounds and diabetic retinopathy, nephropathy, and cardiovascular disease; cardiovascular diseases such as ischemic heart disease, angina pectoris, myocardial ischemia reperfusion injury and infarction, acute and chronic limb ischemia reperfusion injury, congestive heart failure (CHF), atherosclerosis, peripheral arterial hypertension cardiac arrhythmias, idiopathic pulmonary hypertension, pulmonary hypertension associated with idiopathic pulmonary fibrosis, pulmonary hypertension associated with hemolytic disease, primary pulmonary hypertension of the newborn, pulmonary hypertension secondary to congenital diaphragmatic hernia and meconium aspiration; pulmonary hypertension secondary to congenital heart disease; pulmonary hypertension secondary to mitral regurgitation, atrial or ventricular septal defect; contrast-induced nephropathy; asthma; trauma; hypovolemic, neurogenic, or septic shock; idiopathic erectile dysfunction; erectile dysfunction secondary to radical nerve sparing prostatectomy; toxicant-induced inhalational lung injury; chlorine inhalational lung injury; neurotoxicity; neurodegenerative and neurological disorders including Alzheimer and Parkinson's diseases, amyotrophic lateral sclerosis, multiple sclerosis, convulsive (seizure) disorders, AIDS-dementia and disorders which involve processes of learning and memory; glaucoma and intraocular hypertension; disorders of gastric secretions, relaxation and peristalsis of the intestinal tract (including sphincters); drug and disease-induced nephropathies; pathological (premature) and physiological uterine contractions; cellular defense impairment; endothelial dysfunction-induced diseases; insulin-resistance in diabetes; pregnancy-induced hypertension; cerebrovascular diseases; aggregation disorders; and female sexual dysfunction, including vaginal dryness.

The compounds of the present invention allow for more concentrated liquid delivery of the compounds to which they are converted under physiological conditions, as particularly shown with respect to R-107 that is, upon exposure to plasma, converted to R-100 (Example 4 hereinafter). The possibility of delivering smaller volume of the latter may be advantageous in those clinical scenarios where the volume of administration is limiting, e.g., CHF, intramuscular and subcutaneous injections, and all topical applications. As further found while reducing the present invention into practice, the compounds of the present invention are converted to, and release, their corresponding 1-pyrrolidinyloxy, 1-piperidinyloxy and 1-azepanyloxy derivatives, over a defined period of time in biological solutions and tissues. As such, these compounds thereby provide a sustained release of their corresponding 1-pyrrolidinyloxy, 1-piperidinyloxy and 1-azepanyloxy derivatives that is reflected in a lower Cmax in the blood. This may be advantageous in those settings where rapid administration of the latter is undesirable and a sustained release is preferred.

In another aspect, the present invention provides a pharmaceutical composition comprising a compound of the general formula I as defined above, or an enantiomer, diastereomer, racemate, or pharmaceutically acceptable salt or solvate thereof, herein also identified as the active agent, and a pharmaceutically acceptable carrier. Particular such pharmaceutical compositions comprise, as an active agent, a compound selected from the compounds of Tables 2-3 above, e.g., compound $1a_1$, $1a_2$ or $1a_3$, or an enantiomer, diastereomer, racemate, or pharmaceutically acceptable salt or solvate thereof.

The pharmaceutical compositions of the present invention are useful for prevention, treatment or management of a disease, disorder or condition associated with oxidative stress or endothelial dysfunction.

WO 2012/093383 discloses methods and compositions for treatment of sepsis and conditions associated therewith using the 1-pyrrolidinyloxy, 1-piperidinyloxy and 1-azepanyloxy derivatives disclosed in U.S. Pat. Nos. 6,448,267, 6,455,542 and 6,759,430, while particularly exemplifying R-100. Examples 5 and 6 hereinafter describe protocols showing the efficacy of R-107 as a therapeutic agent in mice exposed to a lethal dose of *E. coli* lipopolysaccharide (LPS), and on pulmonary function in sheep suffering from *Pseudomonas aeruginosa*-induced septic pneumonia.

In certain embodiments, the pharmaceutical composition of the invention is thus used for treatment of sepsis, particularly caused by microorganisms or products thereof, and conditions associated therewith. The sepsis may be caused by Gram negative bacteria, e.g., *Escherichia coli, Pseudomonas aeruginosa, Serratia* species, *Salmonella* species, *Shigella* species, *Enterobacter* species, *Citrobacter* species, *Proteus* species, and *Klebsiella* species; Gram-positive cocci, e.g., Pneumococcal species, Enterococcal species, Staphylococcal species, and Streptococcal species; certain fungi and yeast, Rickettsial species, Plasmodial species, Clostridial species, or viruses; or Gram-positive bacterial toxins, including toxic shock syndrome toxins. In particular such embodiments, treatment with the compounds or pharmaceutical compositions of the invention is aimed at inhibiting development of sepsis-related coagulopathy.

The term "treatment" as used herein with respect to sepsis and conditions associated therewith refers to administration of an active agent after the onset of symptoms of sepsis, regardless of the cause for that medical condition. According to the invention, administration of said active agent for treatment of sepsis and conditions associated therewith is aimed at inhibiting, i.e., limiting or reducing, medical conditions resulting from the systemic infection, most particularly pulmonary arterial hypertension, pulmonary shunt, and loss of pulmonary compliance, and in certain cases also development of sepsis-related coagulopathy.

WO 2011/092690 discloses methods and compositions for prevention, treatment, or management of PAH using the 1-pyrrolidinyloxy, 1-piperidinyloxy and 1-azepanyloxy derivatives disclosed in U.S. Pat. Nos. 6,448,267, 6,455,542 and 6,759,430, while particularly exemplifying R-100. Examples 7-9 hereinafter describe protocols showing the efficacy of R-107 as a therapeutic agent in a rat model of PAH, and on monocrotaline (MCT)-induced pulmonary vascular remodeling; a lamb model of pulmonary hypertension of the newborn; and a minipig model of peripheral hypertension, respectively.

In certain embodiments, the pharmaceutical composition of the invention is thus used for prevention, treatment or management of PH, particularly PAH, PH associated with a left heart disease, PH associated with a lung disease and/or hypoxemia, or PH due to a chronic thrombotic and/or embolic disease. The pharmaceutical composition of the invention can be used for treatment any form of PH including, but not limited to, mild, i.e., associated with an increase of up to 30, more particularly 20-30, mmHg in mean pulmonary arterial pressure (MPAP) at rest; moderate, i.e., associated with an increase of 30-39 mmHg in MPAP at rest; and severe, i.e., associated with an increase of 40 mmHg or more in MPAP at rest.

The PAH may be idiopathic PAH; familial PAH; PAH associated with collagen vascular disease; PAH associated with congenital heart disorders; PAH associated with HIV infection; PAH associated with venous or capillary diseases; PAH associated with thyroid disorders, glycogen storage disease, Gaucher's disease, hemoglobinopathies, or myeloproliferative disorders; PAH associated with either smoke inhalation or combined smoke inhalation and burn injury; PAH associated with aspiration; PAH associated with ventilator injury; PAH associated with pneumonia; PAH associated with Adult Respiratory Distress Syndrome; persistent PH of the newborn; neonatal respiratory distress syndrome of prematurity; neonatal meconium aspiration; neonatal diaphragmatic hernia; pulmonary capillary hemangiomatosis; or pulmonary veno-occlusive disease. The left heart disease may be a left sided atrial or ventricular disease; or a valvular disease. The lung disease may be chronic obstructive pulmonary disease; an interstitial lung disease; sleep-disordered breathing; an alveolar hypoventilation disorder; chronic exposure to high altitude; or a developmental lung abnormality. The chronic thrombotic and/or embolic disease may be thromboembolic obstruction of distal or proximal pulmonary arteries; or a non-thrombotic pulmonary embolism of, e.g., tumor cells or parasites.

Many of the diseases, disorders and conditions listed above can be associated with increased risk for PH, wherein particular examples include congenital heart disease, e.g., Eisenmenger syndrome; left heart disease; pulmonary venous disease, e.g., fibrosis tissue narrowing or occluding pulmonary veins and venules; pulmonary arterial disease; diseases causing alveolar hypoxia; fibrotic lung diseases; Williams syndrome; subjects with intravenous drug abuse injury; pulmonary vasculitis such as Wegener's, Goodpasture's, and Churg-Strauss syndromes; emphysema; chronic bronchitis; kyphoscoliosis; cystic fibrosis; obesity-hyperventilation and sleep apnea disorders; pulmonary fibrosis; sarcoidosis; silocosis; CREST (calcinosis cutis, Raynaud phenomenon; esophageal motility disorder; sclerodactyly, and teleangiectasia) and other connective tissue diseases. For example, a subject who possesses a bone morphogenetic protein receptor E (BMPR2) mutation has a 10-20% lifetime risk of acquiring FPAH, and subjects with hereditary hemorrhagic telangiectasa, particularly those carrying mutations in ALKI, were also identified as being at risk for IPAH. Risk factors and diagnostic criteria for PH are described in McGoon et al., *Chest,* 2004, 126, 14S-34S.

The terms "treatment" and "prevention" as used herein with respect to PH refer to administration of an active agent after the onset of symptoms of PH in any of its forms, or prior to the onset of symptoms, particularly to patients at risk for PH, respectively. The term "management" as used herein with respect to PH refers to prevention of recurrence of PH in a patient previously suffered from PH.

WO 2013/005216 discloses methods and compositions for prevention and treatment of renal ischemia-reperfusion injury using the 1-pyrrolidinyloxy, 1-piperidinyloxy and 1-azepanyloxy derivatives disclosed in U.S. Pat. Nos. 6,448, 267, 6,455,542 and 6,759,430, while particularly exemplifying R-100. Example 10 hereinafter describes a protocol showing the efficacy of R-107 as a therapeutic agent in a rat model of renal ischemia-reperfusion injury. In certain embodiments, the pharmaceutical composition of the invention is thus used for prevention or treatment of renal ischemia-reperfusion injury.

The term "renal ischemia" refers to a deficiency of blood flow in one or both kidneys, or nephrons, usually due to functional constriction or actual obstruction of a blood vessel or surgical removal of the kidney. Renal ischemia may result from various medical conditions including, without being limited to, hemorrhagic shock, septic shock, asphyxia also known as asphyxiation, cardiac arrest also known as cardiopulmonary arrest or circulatory arrest, respiratory arrest, respiratory failure, cardiogenic shock, aortic aneurysm, aortic aneurysm surgery, hypotension, dehydration, spinal shock, trauma, cadaveric renal transplantation, living related donor renal transplantation, liver transplantation, a liver disease, drug-induced renal ischemia, hydronephrosis, urethral obstruction, cardiopulmonary bypass surgery, radiocontrast administration, endovascular renal artery catheterization, renovascular stenosis, renal artery thrombosis, ureteral obstruction, hypoxia, and hypoxemia. The term "renal ischemia-reperfusion injury" refers to the damage caused to the kidney(s) when blood supply returns to the tissue after a period of renal ischemia. Renal ischemia-reperfusion injury is characterized by renal dysfunction and tubular damages, and considered as a major cause of acute renal failure that may also be involved in the development and progression of some forms of chronic kidney disease. In general, the absence of oxygen and nutrients from blood during the ischemic period creates a condition in which the restoration of circulation results in inflammation and oxidative damage through the induction of oxidative stress rather than restoration of normal function.

The term "treatment" as used herein with respect to renal ischemia-reperfusion injury refers to administration of an active agent after the onset of symptoms of renal ischemia-reperfusion injury, i.e., after blood supply to the ischemic tissue has been renewed, regardless of the cause for the renal ischemia. The term "prevention" as used herein with respect to renal ischemia-reperfusion injury refers to administration of said active agent prior to the onset of symptoms, i.e., either prior to the onset of renal ischemia or following the onset of renal ischemia but prior to reperfusion, and it is mainly relevant in cases wherein the renal ischemia and/or reperfusion is/are associated with a surgical intervention, e.g., with aortic aneurysm surgery, cadaveric renal transplantation, living related donor renal transplantation, liver transplantation, cardiopulmonary bypass surgery, or endovascular renal artery catheterization. According to the invention, administration of said active agent either for treatment or prevention of renal ischemia-reperfusion injury is aimed at inhibiting, i.e., limiting or reducing, renal dysfunction, PMN infiltration into the renal parenchyma, and histological damage, i.e., tubular necrosis.

Examples 11-12 hereinafter describe protocols showing the efficacy of R-107 as a therapeutic agent in murine and porcine models of retinal ischemia-reperfusion injury. In certain embodiments, the pharmaceutical composition of the invention is thus used for treatment of retinal ischemia-reperfusion injury.

The term "retinal ischemia" refers to those conditions wherein the blood supply to the retinal cells is impaired, resulting in a deficiency of oxygenation to retinal tissue. The term "retinal ischemia-reperfusion injury" refers to those conditions in which retinal ischemia is followed by improved blood flow (so-called "reperfusion"), which thus increases oxidant formation and consequently induces tissue injury.

The term "treatment" as used herein with respect to retinal ischemia-reperfusion injury refers to administration of an active agent after the onset of symptoms of retinal ischemia-reperfusion injury, i.e., after blood supply to the ischemic tissue has been renewed, regardless of the cause for the retinal ischemia. According to the invention, administration of said active agent for treatment of retinal ischemia-reperfusion injury is aimed at inhibiting, i.e., limiting or reducing, the extent of retinal damage and ultimately loss of vision.

Example 13 hereinafter describes a protocol showing the efficacy of R-107 as a therapeutic agent in a rat model of myocardial ischemia-reperfusion injury. In certain embodiments, the pharmaceutical composition of the invention is thus used for prevention or treatment of myocardial ischemia-reperfusion injury.

The term "myocardial ischemia" refers to those conditions in which there is a mismatch of oxygen supply and demand in the myocardium. The term "myocardial ischemia-reperfusion injury" refers to those settings where revascularization of an ischemic region of the heart is accompanied by an increased flux of free radicals and the subsequent evolution of myocardial tissue damage.

The term "treatment" as used herein with respect to myocardial ischemia-reperfusion injury refers to administration of an active agent after the onset of symptoms of myocardial ischemia-reperfusion injury, i.e., after blood supply to the ischemic tissue has been renewed, regardless of the cause for the myocardial ischemia. The term "prevention" as used herein with respect to myocardial ischemia-reperfusion injury refers to administration of said active agent prior to the onset of symptoms, i.e., either prior to the onset of myocardial ischemia or following the onset of myocardial ischemia but prior to reperfusion, and it is mainly relevant in cases wherein an acute therapeutic revascularization event is undertaken, such as angioplasty or thrombolysis. According to the invention, administration of said active agent either for treatment or prevention of myocardial ischemia-reperfusion injury is aimed at inhibiting, i.e., limiting or reducing, the extent of devitalized myocardium and the appearance of arrhythmias.

Example 14 hereinafter describes a protocol showing the efficacy of R-107 as a therapeutic agent in a minipig model of acute limb ischemia-reperfusion injury. In certain embodiments, the pharmaceutical composition of the invention is thus used for prevention or treatment of limb ischemia-reperfusion injury.

The term "limb ischemia" refers to a mismatch in the supply and demand of oxygen to an extremity. The term "limb ischemia-reperfusion injury" refers to the injury resulting from an acute restoration of blood flow to a previously ischemic extremity.

The term "treatment" as used herein with respect to limb ischemia-reperfusion injury refers to administration of an active agent after the onset of symptoms of limb ischemia-reperfusion injury, i.e., after blood supply to the ischemic tissue has been renewed, regardless of the cause for the limb ischemia. The term "prevention" as used herein with respect to limb ischemia-reperfusion injury refers to administration of said active agent prior to the onset of symptoms, i.e., either prior to the onset of limb ischemia or following the onset of limb ischemia but prior to reperfusion, and it is mainly relevant in cases wherein restoration of blood flow to the affected limb takes place within 6-12 hours of acute ischemia. According to the invention, administration of said active agent either for treatment or prevention of limb ischemia-reperfusion injury is aimed at inhibiting, i.e., limiting or reducing, muscle damage, muscle weakness, limb necrosis and gangrene, limb amputation, myoglobinuria, renal failure, compartment syndrome, hyperkalemia, acute respiratory distress syndrome, and circulatory shock.

Example 15 hereinafter describes a protocol showing the efficacy of R-107 as a therapeutic agent in a rat model of contrast-induced nephropathy. In certain embodiments, the pharmaceutical composition of the invention is thus used for prevention or treatment of contrast-induced nephropathy.

The term "contrast-induced nephropathy" refers to the impairment of renal morphology and function resulting from the acute administration of a radio-opaque dye for purposes of angiography, with said nephropathy typically occurring in the setting of underlying renal disease, as reflected by a reduced glomerular filtration rate and tubular function and elevated serum blood urea nitrogen (BUN) and/or creatinine.

The terms "treatment" and "prevention" as used herein with respect to contrast-induced nephropathy refer to administration of an active agent after the onset of symptoms of contrast-induced nephropathy, or prior to the onset of symptoms, respectively. According to the invention, administration of said active agent either for treatment or prevention of contrast-induced nephropathy is aimed at ensuring the vitality of the kidney, as reflected by morphologic assessment and functional measures of glomerular filtration and tubular behavior, such as serum BUN and creatinine.

WO 2013/190497 discloses methods and compositions for treatment of CILI using, inter alia, the 1-pyrrolidinyloxy, 1-piperidinyloxy and 1-azepanyloxy derivatives disclosed in U.S. Pat. Nos. 6,448,267, 6,455,542 and 6,759,430, while particularly exemplifying R-100. Example 16 hereinafter shows the efficacy of R-107 as a therapeutic agent in a murine $Cl_2$ exposure model.

In certain embodiments, the pharmaceutical composition of the invention is thus used for treatment of an inflammatory disease of the lung caused by inhalation of a toxic agent or an irritant. In one particular such embodiment, the toxic agent is $Cl_2$, and the pharmaceutical composition is used for treatment of CILI. In another particular such embodiments, the toxic agent is the chemical warfare agent phosgene or diphosgene, or the irritant is smoke.

The term "treatment", as used herein with respect to an inflammatory diseases of the lung caused by inhalation of a toxic agent or an irritant, refers to administration of an active agent after exposure to said toxic agent or irritant and following the onset of symptoms of said inflammatory disease, so as to ameliorate the effects of said toxic agent or irritant on the lungs. According to the invention, administration of said active agent for treatment of CILI is aimed at reducing pulmonary edema and pulmonary shunt, diminishing PMN infiltration into the lung parenchyma, inhibiting a loss in pulmonary compliance, improving oxygenation, and decreasing carbon dioxide retention.

Example 17 hereinafter describes a protocol showing the efficacy of R-107 as a therapeutic agent in a rat model of erectile dysfunction. In certain embodiments, the pharmaceutical composition of the invention is thus used for treatment of erectile dysfunction.

The term "erectile dysfunction" refers to the inability of a male to produce an erection that allows for reliable and effective penetration of the vagina. The term "treatment" as used herein with respect to erectile dysfunction refers to administration of an active agent after the onset of symptoms of erectile dysfunction. According to the invention, administration of said active agent for treatment of erectile dysfunction is aimed at improving erectile quality and thereby facilitating successful vaginal penetration.

The pharmaceutical compositions of the present invention can be provided in a variety of formulations, e.g., in a pharmaceutically acceptable form and/or in a salt form, as well as in a variety of dosages.

In one embodiment, the pharmaceutical composition of the present invention comprises a non-toxic pharmaceutically acceptable salt of a compound of the general formula I. Suitable pharmaceutically acceptable salts include acid addition salts such as, without being limited to, the mesylate salt, the maleate salt, the fumarate salt, the tartrate salt, the hydrochloride salt, the hydrobromide salt, the esylate salt, the p-toluenesulfonate salt, the benzenesulfonate salt, the benzoate salt, the acetate salt, the phosphate salt, the sulfate salt, the citrate salt, the carbonate salt, and the succinate salt. Additional pharmaceutically acceptable salts include salts of ammonium ($NH_4^+$) or an organic cation derived from an amine of the formula $R_4N^+$, wherein each one of the Rs independently is selected from H, $C_1$-$C_{22}$, preferably $C_1$-$C_6$ alkyl, such as methyl, ethyl, propyl, isopropyl, n-butyl, sec-butyl, isobutyl, tert-butyl, n-pentyl, 2,2-dimethylpropyl, n-hexyl, and the like, phenyl, or heteroaryl such as pyridyl, imidazolyl, pyrimidinyl, and the like, or two of the Rs together with the nitrogen atom to which they are attached form a 3-7 membered ring optionally containing a further heteroatom selected from N, S and O, such as pyrrolydine, piperidine and morpholine. Furthermore, where the compounds of the general formula I carry an acidic moiety, suitable pharmaceutically acceptable salts thereof may include metal salts such as alkali metal salts, e.g., lithium, sodium or potassium salts, and alkaline earth metal salts, e.g., calcium or magnesium salts.

Further pharmaceutically acceptable salts include salts of a cationic lipid or a mixture of cationic lipids. Cationic lipids are often mixed with neutral lipids prior to use as delivery agents. Neutral lipids include, but are not limited to, lecithins; phosphatidylethanolamine; diacyl phosphatidylethanolamines such as dioleoyl phosphatidylethanolamine, dipalmitoyl phosphatidylethanolamine, palmitoyloleoyl phosphatidylethanolamine and distearoyl phosphatidyletha-
nolamine; phosphatidylcholine; diacyl phosphatidylcholines such as dioleoyl phosphatidylcholine, dipalmitoyl phosphatidylcholine, palmitoyloleoyl phosphatidylcholine and distearoyl phosphatidylcholine; phosphatidylglycerol; diacyl phosphatidylglycerols such as dioleoyl phosphatidylglycerol, dipalmitoyl phosphatidylglycerol and distearoyl phosphatidylglycerol; phosphatidylserine; diacyl phosphatidylserines such as dioleoyl- or dipalmitoyl phosphatidylserine; and diphosphatidylglycerols; fatty acid esters; glycerol esters; sphingolipids; cardiolipin; cerebrosides; ceramides; and mixtures thereof. Neutral lipids also include cholesterol and other 3β hydroxy-sterols.

Examples of cationic lipid compounds include, without being limited to, Lipofectin® (Life Technologies, Burlington, Ontario) (1:1 (w/w) formulation of the cationic lipid N-[1-(2,3-dioleyloxy)propyl]-N,N,N-trimethylammonium chloride and dioleoylphosphatidyl-ethanolamine); Lipofectamine™ (Life Technologies, Burlington, Ontario) (3:1 (w/w) formulation of polycationic lipid 2,3-dioleyloxy-N-[2(spermine-carboxamido)ethyl]-N,N-dimethyl-1-propanamin-iumtrifluoroacetate and dioleoylphosphatidyl-ethanolamine), Lipofectamine Plus (Life Technologies, Burlington, Ontario) (Lipofectamine and Plus reagent), Lipofectamine 2000 (Life Technologies, Burlington, Ontario) (Cationic lipid), Effectene (Qiagen, Mississauga, Ontario) (Non liposomal lipid formulation), Metafectene (Biontex, Munich, Germany) (Polycationic lipid), Eu-fectins (Promega Biosciences, San Luis Obispo, Calif.) (ethanolic cationic lipids numbers 1 through 12: $C_{52}H_{106}N_6O_4 \cdot 4CF_3CO_2H$, $C_{88}H_{178}N_8O_4S_2 \cdot 4CF_3CO_2H$, $C_{40}H_{84}NO_3P \cdot CF_3CO_2H$, $C_{50}H_{103}N_7O_3 \cdot 4CF_3CO_2H$, $C_{55}H_{116}N_8O_2 \cdot 6CF_3CO_2H$, $C_{49}H_{102}N_6O_3 \cdot 4CF_3CO_2H$, $C_{44}H_{89}N_5O_3 \cdot 2CF_3CO_2H$, $C_{100}H_{206}N_{12}O_4S_2 \cdot 8CF_3CO_2H$, $C_{162}H_{330}N_{22}O_9 \cdot 13CF_3CO_2H$, $C_{43}H_{88}N_4O_2 \cdot 2CF_3CO_2H$, $C_{43}H_{88}N_4O_3 \cdot 2CF_3CO_2H$, $C_{41}H_{78}NO_8P$); Cytofectene (Bio-Rad, Hercules, Calif.) (mixture of a cationic lipid and a neutral lipid), GenePORTER® (Gene Therapy Systems, San Diego, Calif.) (formulation of a neutral lipid (Dope) and a cationic lipid) and FuGENE 6 (Roche Molecular Biochemicals, Indianapolis, Ind.) (Multi-component lipid based non-liposomal reagent).

The pharmaceutically acceptable salts of the present invention may be formed by conventional means, e.g., by reacting a free base form of the active agent, i.e., the compound of the general formula I, with one or more equivalents of the appropriate acid in a solvent or medium in which the salt is insoluble, or in a solvent such as water which is removed in vacuo or by freeze drying, or by exchanging the anion/cation of an existing salt for another anion/cation on a suitable ion exchange resin.

The present invention encompasses solvates of the compounds of the general formula I as well as salts thereof, e.g., hydrates.

The pharmaceutical compositions provided by the present invention may be prepared by conventional techniques, e.g., as described in Remington: The Science and Practice of Pharmacy, $19^{th}$ Ed., 1995. The compositions can be prepared, e.g., by uniformly and intimately bringing the active agent into association with a liquid carrier, a finely divided solid carrier, or both, and then, if necessary, shaping the product into the desired formulation. The compositions may be in liquid, solid or semisolid form and may further include pharmaceutically acceptable fillers, carriers, diluents or adjuvants, and other inert ingredients and excipients. In one embodiment, the pharmaceutical composition of the present invention is formulated as nanoparticles.

The compositions can be formulated for any suitable route of administration, but they are preferably formulated for parenteral, e.g., intravenous, intraarterial, intramuscular, intraperitoneal, intrathecal, intrapleural, intratracheal, subcutaneous, or topical administration, as well as for inhalation. Pharmaceutical compositions formulated for intramuscular injections may be suitable, inter alia, for emergent use such as in CILI; and pharmaceutical compositions formulated for topical administration may be suitable, inter alia, for treatment of skin ulcers and wounds, elevated intraocular pressure and uveitis (by application to the cornea), and erectile dysfunction (by application to the penile), as well as for increasing genital lubrication (by vaginal application). The dosage will depend on the state of the patient, and will be determined as deemed appropriate by the practitioner.

The pharmaceutical composition of the invention may be in the form of a sterile injectable aqueous or oleagenous suspension, which may be formulated according to the known art using suitable dispersing, wetting or suspending agents. The sterile injectable preparation may also be a sterile injectable solution or suspension in a non-toxic parenterally acceptable diluent or solvent. Acceptable vehicles and solvents that may be employed include, without limiting, water, Ringer's solution, polyethylene glycol (PEG), 2-hydroxypropyl-β-cyclodextrin (HPCD), Tween-80, and isotonic sodium chloride solution.

Pharmaceutical compositions according to the present invention, when formulated for inhalation, may be administered utilizing any suitable device known in the art, such as metered dose inhalers, liquid nebulizers, dry powder inhalers, sprayers, thermal vaporizers, electrohydrodynamic aerosolizers, and the like.

Pharmaceutical compositions according to the present invention, when formulated for administration route other than parenteral administration, may be in a form suitable for oral use, e.g., as tablets, troches, lozenges, aqueous, or oily suspensions, dispersible powders or granules, emulsions, hard or soft capsules, or syrups or elixirs.

Pharmaceutical compositions intended for oral administration should be formulated so as to inhibit the release of the active agent in the stomach, i.e., delay the release of the active agent until at least a portion of the dosage form has traversed the stomach, in order to avoid the acidity of the gastric contents from hydrolyzing the active agent to its highly water insoluble form, i.e., its corresponding 1-pyrrolidinyloxy, 1-piperidinyloxy or 1-azepanyloxy derivative. Particular such compositions are those wherein the active agent is coated by a pH-dependent enteric-coating polymer. Examples of pH-dependent enteric-coating polymer include, without being limited to, Eudragit® S (poly(methacrylicacid, methylmethacrylate), 1:2), Eudragit® L 55 (poly (methacrylicacid, ethylacrylate), 1:1), Kollicoat® (poly (methacrylicacid, ethylacrylate), 1:1), hydroxypropyl methylcellulose phthalate (HPMCP), alginates, carboxymethylcellulose, and combinations thereof. The pH-dependent enteric-coating polymer may be present in the composition in an amount from about 10% to about 95% by weight of the entire composition.

Pharmaceutical compositions intended for oral administration may be prepared according to any method known to the art for the manufacture of pharmaceutical compositions and may further comprise one or more agents selected from sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be, e.g., inert diluents such as calcium carbonate, sodium carbonate, lactose, calcium phosphate, or sodium phosphate; granulating and disintegrating agents, e.g., corn starch or alginic acid; binding agents, e.g., starch, gelatin or acacia; and lubricating agents, e.g., magnesium stearate, stearic acid, or talc. The tablets may be either uncoated or coated utilizing known techniques to delay disintegration and absorption in the gastrointestinal tract and thereby provide a sustained action over a longer period. For example, a time delay material such as glyceryl monostearate or glyceryl distearate may be employed. They may also be coated using the techniques described in the U.S. Pat. Nos. 4,256,108, 4,166,452 and 4,265,874 to form osmotic therapeutic tablets for control release. The pharmaceutical composition of the invention may also be in the form of oil-in-water emulsion.

The pharmaceutical compositions of the invention may be formulated for controlled release of the active agent. Such compositions may be formulated as controlled-release matrix, e.g., as controlled-release matrix tablets in which the release of a soluble active agent is controlled by having the active diffuse through a gel formed after the swelling of a hydrophilic polymer brought into contact with dissolving liquid (in vitro) or gastro-intestinal fluid (in vivo). Many polymers have been described as capable of forming such gel, e.g., derivatives of cellulose, in particular the cellulose ethers such as hydroxypropyl cellulose, hydroxymethyl cellulose, methylcellulose or methyl hydroxypropyl cellulose, and among the different commercial grades of these ethers are those showing fairly high viscosity. In other configurations, the compositions comprise the active agent formulated for controlled release in microencapsulated dosage form, in which small droplets of the active agent are surrounded by a coating or a membrane to form particles in the range of a few micrometers to a few millimeters.

Another contemplated formulation is depot systems, based on biodegradable polymers, wherein as the polymer degrades, the active ingredient is slowly released. The most common class of biodegradable polymers is the hydrolytically labile polyesters prepared from lactic acid, glycolic acid, or combinations of these two molecules. Polymers prepared from these individual monomers include poly (D,L-lactide) (PLA), poly (glycolide) (PGA), and the copolymer poly (D,L-lactide-co-glycolide) (PLG).

In a further aspect, the present invention relates to a compound of the general formula I as defined above, or an enantiomer, diastereomer, racemate, or pharmaceutically acceptable salt or solvate thereof, for use in prevention, treatment or management of a disease, disorder or condition associated with oxidative stress or endothelial dysfunction.

In yet another aspect, the present invention relates to use of a compound of the general formula I as defined above, or an enantiomer, diastereomer, racemate, or pharmaceutically acceptable salt or solvate thereof, for the preparation of a pharmaceutical composition for prevention, treatment or management of a disease, disorder or condition associated with oxidative stress or endothelial dysfunction.

In still another aspect, the present invention relates to a method for prevention, treatment or management of a disease, disorder or condition associated with oxidative stress or endothelial dysfunction in an individual in need thereof, comprising administering to said individual an effective amount of a compound of the general formula I as defined above, or an enantiomer, diastereomer, racemate, or pharmaceutically acceptable salt or solvate thereof.

In one particular embodiment, the method of the present invention is for treatment of CILI.

The invention will now be illustrated by the following non-limiting Examples.

EXAMPLES

Experimental

Synthesis of 3-nitrooxymethyl-proxyl

A suspension of 3-carboxyproxyl (77.5 g, 0.416 mol) in dry tetrahydrofuran (THF, 500 ml) was cooled to 0° C. Lithium aluminum hydride (2M solution in THF, 160 ml, 0.32 mol) was slowly added to the suspension over 4 hours under nitrogen atmosphere. During the addition, the temperature was maintained below 5° C. After the completion of addition, the reaction mixture was stirred at 0-5° C. for 30 minutes and then at room temperature for 3 hours. The reaction mixture was again cooled to 0° C. Sodium sulfate decahydrate solid (52 gm) was slowly added in small portions over 1 hour. The suspension was stirred further for 1 hour. It was diluted with ethyl acetate (1 liter) and filtered. The cake was washed with ethyl acetate (500 ml) and the filtrate was concentrated on rotary evaporator. The residue obtained after concentration was suspended in 30% ethyl acetate-hexane (500 ml), and the solid separated out was filtered and washed with 30% ethyl acetate-hexane and dried under vacuum to give 3-hydroxymethyl-proxyl as yellow colored solid (56.320 g). The material was used as such for next reaction. Concentrated nitric acid (90% solution, 100 ml) was cooled to 0° C. using ice bath in 2 liter beaker. Concentrated sulfuric acid (100 ml) was slowly added to nitric acid at 0° C. over 15 minutes. The mixture was stirred at 0-50° C. for 15 minutes. 3-Hydroxymethyl-proxyl (50 g, 0.29 mol) was added in small portions over 2 hours. After the addition, the mixture was stirred at 0-5° C. for 1 hour, and quenched with crushed ice (~1 kg). The mixture was then basified by slow addition of solid potassium carbonate (460 g) over 1 hour at 0° C. The basic mixture was stirred at room temperature for 30 minutes. The solid separated out was filtered and washed with water (1 liter). The solid was re-suspended in water (400 ml) and ethyl acetate (400 ml) added, and the biphasic mixture was transferred into a separatory funnel. The ethyl acetate layer was collected. Aqueous layer was extracted again with ethyl acetate (400 ml). The combined organic extract was dried on anhydrous sodium sulfate and filtered. The filtrate was concentrated on rotary evaporator. The residue was dissolved ethyl acetate and triturated with hexane. The solid separated out was collected by filtration to produce 3-nitrooxymethyl-proxyl as pale yellow solid (39.7 g). MS (ES$^+$): m/z 218.3 (M+1).

Synthesis of (1-hydroxy-2,2,5,5-tetramethylpyrrolidin-3-yl)methyl nitrate hydrochloride A suspension of 3-nitrooxymethyl-proxyl (10.0 g, 0.046 mol) in ethanol (100 ml) was slowly treated with 4 M solution of hydrochloric acid in dioxane (0.1 mol) at room temperature. The reaction mixture was then stirred for 2 hours and concentrated on rotary evaporator. Dry ether was added and the solid separated out was filtered and dried under vacuum to give (1-hydroxy-2,2,5,5-tetramethylpyrrolidin-3-yl)methyl nitrate hydrochloride as white solid (11.050 g). $^1$H NMR (DMSO-d$_6$): δ 1.19-1.51 (m, 12H), 2.02 (m, 1H), 2.48-2.52 (m, 1H), 3.45 (m, 1H), 4.56-4.66 (m, 2H), 11.52 (bs, 1H), 11.86 (bs, 1H). MS (ES$^+$): m/z 219.3 (M+1).

Example 1. Synthesis of [1-(acetyloxy)-2,2,5,5-tetramethylpyrrolidin-3-yl] methyl nitrate, 1a$_1$ (R-107)

1-Hydroxy-2,2,5,5-tetramethylpyrrolidin-3-yl)methyl nitrate hydrochloride (4.0 g, 0.0157 mol) was dissolved in THF (40 ml) and treated with triethylamine (4.5 ml) and acetic anhydride (2 ml) at room temperature for 1 hour. The reaction mixture was concentrated and dissolved in ethyl acetate and water (50 ml each). Organic layer was collected and dried over sodium sulfate. It was concentrated and the residue was purified on silica gel column using 0-20% ethyl acetate-hexane to give (1-acetoxy-2,2,5,5-tetramethylpyrrolidin-3-yl)methyl nitrate as pale yellow oil (4.1 g). $^1$H NMR (CDCl$_3$): δ 1.10 (s, 3H), 1.15 (s, 3H), 1.18 (s, 3H), 1.21 (s, 3H), 1.59-1.65 (m, 1H), 1.88-1.93 (dd, J=7 and 12 Hz, 1H), 2.11 (s, 3H), 2.37-2.41 (m, 1H), 4.36-4.51 (m 2H).

Example 2. Synthesis of [(1-propanoyloxy-2,2,5,5-tetramethylpyrrolidin-3-yl)] methyl nitrate, 1a$_2$ 1-Hydroxy-2,2,5,5-tetramethylpyrrolidin-3-yl)methyl nitrate hydrochloride (1.0 g, 0.004 mol) was dissolved in THF (20 ml) and treated with triethylamine (3 eq) and propionic anhydride (2 eq) at room temperature for 1 hour. The reaction mixture was concentrated and dissolved in ethyl acetate and water (50 ml each). The organic layer was collected and dried over sodium sulfate. It was concentrated and the residue was purified on silica gel column using 0-20% ethyl acetate-hexane to give (1-propanoyloxy-2,2,5-tetramethyl pyrrolidin-3-yl)methyl nitrate as pale yellow oil (1.010 g). $^1$H NMR (CDCl$_3$): δ 1.09 (s, 3H), 1.16 (s, 3H), 1.17 (s, 3H), 1.18-1.21 (m, 6H), 1.58-1.65 (m, 1H), 1.85-1.92 (dd, J=7.5 and 12.9 Hz, 1H), 2.33-2.41 (m, 2H), 2.37-2.41 (m, 1H), 4.34-4.50 (m 2H).

Example 3. Synthesis of [1-(2-methylpropanoyloxy-2,2,5,5-tetramethyl pyrrolidin-3-yl)]methyl nitrate, 1a$_3$ 1-Hydroxy-2,2,5,5-tetramethylpyrrolidin-3-yl)methyl nitrate hydrochloride (1.04 g, 0.004 mol) was dissolved in THF (20 ml) and treated with triethylamine (3 eq) and isobutyryl anhydride (1.5 eq) at room temperature for 30 minutes. The reaction mixture was concentrated and dissolved in ethyl acetate and water (50 ml each). Organic layer was collected and dried over sodium sulfate. It was concentrated and the residue was purified on silica gel column using 25% ethyl acetate-hexane to give [1-(2-methylpropanoyloxy-2,2,5,5-tetramethylpyrrolidin-3-yl)]methyl nitrate as pale yellow oil (1.0 g). $^1$H NMR (CDCl$_3$): δ 1.10-1.22 (m, 18H), 1.61 (dd, J=12 Hz, 1H), 1.85-1.92 (dd, J=7.5 and 12 Hz, 1H), 2.33-2.43 (m, 1H), 2.57-2.67 (m, 1H), 4.38-4.51 (m, 2H).

Example 4. R-107 is Converted Under Physiological Conditions to R-100

In an in vitro study, 2,2,5,5-tetramethyl-3-(nitrooxymethyl)pyrrolidin-1-yl acetate (R-107) was incubated in mouse or rat plasma at 37° C. at a concentration of 4 mM, and the relative concentrations of this compound as well as of its corresponding hydroxylamine, (1-hydroxy-2,2,5,5-tetramethylpyrrolidin-3-yl) methyl nitrate (R-105), and 3-nitratomethyl-2,2,5,5-tetramethylpyrrolidinyloxy (R-100), were measured by HPLC. Table 4 shows the relative concentration of each one of the compounds in mouse and rat plasma following 0.1, 1.5 and 20 hours, indicating that R-107 is, in fact, a prodrug of its corresponding hydroxylamine compound upon hydrolysis of the ester bond (O—C(O)R$_3$ in the general formula I), wherein the hydroxylamine compound is then oxidized, in vivo, to its corresponding nitroxide derivative R-100.

TABLE 4

Relative concentrations of R-107, R-105 and R-100 upon incubation of R-107 in mouse or rat plasma

| | Mouse Concentration | | | Rat Concentration | | |
|---|---|---|---|---|---|---|
| Time (hrs) | R-100 | R-105 | R-107 | R-100 | R-105 | R-107 |
| 0.1 | 0 | 0 | 326 | 8 | 68 | 246 |
| 1.5 | 91 | 61 | 284 | 26 | 159 | 18 |
| 20 | 260 | 32 | 0 | 195 | 29 | 0 |

In the following two experiments, the pharmacokinetic of releasing R-100 from R-107, via R-105 that is the reduced form of R-100, was studied in vivo according to the protocol described herein.

Methods and Standards

100 μl aliquots plasma obtained from R-107-treated sheep or pig were thawed and 200 μl ice-cold ethanol was added to each 100 μl sample to precipitate protein. Samples were then vortexed, placed on ice for 10 minutes, and then spun down at room temperature for 15 minutes. A first 100 μl supernatant from each spun sample was withdrawn and placed in a labeled HPLC micro vial to which 300 μl MPA (LC mobile phase A) was added, and the vial contents were then mixed and submitted for LCMS analysis (kept at 4° C.). The concentration of R-107 was measured in this sample as was the concentration of R105. A second 100 μl supernatant from each spun sample was added to a labelled HPLC micro vial to which 300 μl MPA and 2 μl of Reducing solution (ascorbic acid, 1.0 mg/ml in water) were added. These vials were vortexed; incubated at 50° C. for 1 hour with gentle shaking; and were then cooled to 4° C. and submitted for LCMS analysis. This sample was analyzed for R105, i.e., reduced form of R-100, and the amount measured thus represents the sum of R-100 and R-105 originally present in the plasma. The concentration of R-100 can be calculated from that of the R-105 in the second sample minus that of R-105 in the first sample. However, the concentrations of R-105 were seen to be low (approximately 10% or less of those of R-100) and so the results reported below as R-100 are not corrected for R-105.

Sets of standards (R-100, R-105 and R-107) were prepared by spiking individually in pig plasma. 100 μl aliquots of these spiked plasma samples, after thawing, were included in the above extraction protocol.

Analysis Methods

Analysis method were carried out with an Agilent HPLC stack, with column eluate directed, via a diverter valve, into the source of an AB Sciex 'Qstar Elite' Hybrid TOF, high-resolution mass spectrometer. LC column: Phenomenex Kinetex C18 2.6 u 100 A, 2.1×50 mm. LC mobile phase A: H$_2$O with 0.02% trifluoroacetic acid (TFA), 0.1% formic acid (HOF); Phase B: acetonitrile (ACN) with 0.02% TFA, 0.1% HOF. Mobile phase flow rate=500 μl/min. Injection size: 8 μl, via Agilent 1100 u-WPS autosampler.

Tables 5 and 6 show the amount of R-107 and R-100 measured in the plasma of a sheep (35 kg) at certain points in time following IV or IM administration, respectively, of neat R-107 (0.8 ml, 880 mg, 25 mg/kg) over 10 minutes. For the purpose of comparison, Table 7 shows the amount of R-100 measured at certain points in time following IV administration of R-100 in HPCD (20 mg/ml), 20 mg/kg bolus (the ratio between the molecular weights of R-107: R-100 is 269:217, so the dosing of 25 mg/kg and 20 mg/kg, R-107:R-100, is approximately equimolar).

TABLE 5

IV injection of neat R-107 to sheep

| Time post dose (hrs) | R-100 μg/ml | R-107 μg/ml |
|---|---|---|
| 0 | 0 | 0 |
| 0.1 | 12.04 | 5.5 |
| 0.4 | 8.87 | 1.21 |
| 0.5 | 7.10 | 0.2 |
| 1 | 3.14 | 0 |
| 2 | 1.25 | not detected |
| 4 | 0.43 | not detected |
| 6 | 0.18 | not detected |
| 8 | 0.12 | not detected |
| 24 | 0.06 | not detected |

TABLE 6

IM injection of neat R-107 to sheep (no R-107 was detected)

| Time post dose (hrs) | R-100 μg/ml |
|---|---|
| 0 | — |
| 0.25 | 0.14 |
| 0.5 | 0.2 |
| 1 | 0.3 |
| 2 | 0.32 |
| 4 | 0.38 |
| 8 | 0.33 |
| 24 | 0.17 |
| 48 | not detected |

TABLE 7

IV injection of neat R-100 to sheep (20 mg/kg bolus)

| Time post dose (hrs) | R-100 μg/ml |
|---|---|
| 0 | 0 |
| 0.08 | 6.72 |
| 0.17 | 6.11 |
| 0.25 | 5.31 |
| 0.5 | 2.72 |
| 1 | 1.63 |
| 2 | 0.7 |
| 4 | 0.28 |
| 8 | 0.03 |

Table 8 shows the amount of R-107 and R-100 measured in the plasma of a pig (10 kg) at certain points in time following IV administration of neat R-107 (0.8 ml, 880 mg, 88 mg/kg) over 6 minutes; Table 9 shows the amount of R-107 and R-100 measured in the plasma of a pig (10 kg) at certain points in time following IV administration of R-107 diluted in 4 parts of PEG400 (0.8 ml, 176 mg, 18 mg/kg) over 6 minutes; and Table 10 shows the amount of R-107 and R-100 measured in the plasma of a pig (10 kg) at certain points in time following oral administration of neat R-107 (0.8 ml, 880 mg, 88 mg/kg; given as a capsule per os).

TABLE 8

IV injection of neat R-107 to pig

| Time post dose (hrs) | R-107 µg/ml | R-100 µg/ml |
| --- | --- | --- |
| −0.08 | 0 | 0 |
| 0.08 | 5.24 | 16.03 |
| 0.17 | 5.87 | 15.50 |
| 0.25 | 3.43 | 16.63 |
| 0.5 | 1.32 | 16.76 |
| 1 | 0.36 | 13.63 |
| 2 | 0.26 | 7.36 |
| 6 | not detected | 0.70 |
| 24 | not detected | 0.03 |

TABLE 9

IV injection of R-107 diluted in 4 parts of PEG400 to pig

| Time post dose (hrs) | R-107 µg/ml | R-100 µg/ml |
| --- | --- | --- |
| −0.08 | 0 | 0 |
| 0.08 | 2.38 | 5.83 |
| 0.17 | 0.64 | 5.76 |
| 0.25 | 0.43 | 4.88 |
| 0.5 | 0.25 | 3.84 |
| 1 | 0.22 | 2.50 |
| 2 | not detected | 1.72 |
| 4 | not detected | 0.78 |
| 8 | not detected | 0.20 |
| 24 | not detected | not detected |

TABLE 10

Capsule (per os) of neat R-107 to pig (0.8 ml, 88 mg/kg)

| Time post dose (hrs) | R-107 ng/ml | R-100 ng/ml |
| --- | --- | --- |
| −0.08 | — | — |
| 0.08 | 1.319 | 0.964 |
| 0.17 | 0.715 | 1.504 |
| 0.5 | 0.345 | 1.424 |
| 1 | 0.11 | 1.257 |
| 2 | 0.222 | 0.609 |
| 3 | 0.11 | 1.607 |
| 4 | 0.122 | 2.031 |
| 8 | not detected | 0.387 |
| 24 | not detected | not detected |

Example 5. R-107 is Effective in a Murine Model of Sepsis

In this study, Balb/c mice exposed to a lethal dose of *E. coli* lipopolysaccharide (LPS; 10 mg/kg IP) are treated with R-107 (0, 20, 40, or 80 mg/kg/day, BID IP), with the initial dose given 1 hour after LPS injection, and the mortality for the animal treated with LPS only (the control group) vs. that for the animals treated with the various doses of R-107 is compared.

In a satellite study, tissues and sera are collected at 16 hours, i.e., 15 hours after the first administration and 3 hours after the second administration of R-107, for analysis, and the level of creatinine, aspartate transaminase (AST), alanine transaminase (ALT), bilirubin, amylase, lipase, and alkaline phosphatase (ALP), associated with kidney, pancreas, and liver functioning are measured.

Similar studies may be conducted with compounds of the general formula I other than R-107.

Example 6. R-107 is Effective in a Sheep Model of Septic Pneumonia

In this study, a model of sheep suffering from *Pseudomonas aeruginosa* (PSA)-induced septic pneumonia and consequent pulmonary dysfunction is used. Female Merino sheep are operatively instrumented for chronic study with Swan-Ganz®, i.e., pulmonary artery, and femoral artery catheters, and are randomly allocated to vehicle control or R-107 treatment group. Smoke inhalation injury (48 breaths of cotton smoke) is induced and $2.4 \times 10^{11}$ colony-forming units (CFU) of PSA are instilled in the lung via bronchoscope under general anesthesia. The animal in the treatment group are intravenously (IV) administered with a total of 80 mg/kg of R-107 BID. Ringer's lactate solution is titrated IV to maintain hematocrit (hct) at baseline±3%. Measurements are taken at baseline and every 3 hours during the 24 hours study period. Data are expressed as mean±SEM. Statistical analysis: two-way ANOVA and Bonferroni post hoc comparison. A p-value <0.05 is considered as statistically significant.

Similar studies may be conducted with compounds of the general formula I other than R-107.

Example 7. The Effect of R-107 on MCT-Induced Changes in Systemic and Pulmonary Arterial Pressure, and on MCT-Induced Pulmonary Vascular Remodeling In this study, adult male Sprague-Dawley rats (250-350 g) (3 groups) are treated with a single subcutaneous injection of monocrotaline (MCT; 60 mg/kg), a plant poison that induces a well-characterized experimental model of pulmonary hypertension, or an equivalent volume of saline (2 ml/kg; vehicle, control). After a period of 38 days in which rats develop severe PAH, dosing with R-107 for 10 days is initiated, as follows: group 1 (sham animals) does not receive MCT and is dosed with vehicle control in drinking water; group 2 is dosed with vehicle control in drinking water; group 3 is dosed with R-107 (80-160 mg/kg/day, BID IP). At the conclusion of the 10-day dosing period, rats are anesthetized and instrumented, and resting hemodynamic indices are recorded.

At post-mortem, the lower lobe of the right lung is fixed with formalin solution, and after paraffin embedding, 5 mm sections are stained with haematoxylin and eosin and observed in a Dialux 22 Leitz (Wetziar, Germany) microscope. The score of lung fibrosis is assessed on sections stained with Masson Trichrome staining. For morphometric evaluations, all three lobes of right lung are inspected. For each lobe the vessels of medium and small size that demonstrate edema and inflammatory cells are counted. Results are expressed as the percentage of vessels presenting indices of disease relative to the total number of vessels counted in the sections. The percentage of vessels demonstrating thickening of the layer of smooth muscle in the tunica are also expressed as a percentage relative to the total number of vessels counted.

Similar studies may be conducted with compounds of the general formula I other than R-107.

Example 8. R-107 is Effective in a Lamb Model of Pulmonary Hypertension of the Newborn In this study, a prospective, placebo-controlled, dose-escalation, randomized study is carried out in anesthetized, mechanically-ventilated, and muscle-relaxed newborn lambs wherein pulmonary hypertension of the newborn (PPHN) has been induced by in utero ligation of the ductus arteriosus. This clinically-relevant gold-standard model is characterized by severe PAH that is poorly responsive to inhaled nitric oxide (iNO), thus reflecting the 30-50% of clinical PPHN non-responders to clinical iNO therapy. R-107 (0, 0.3, 1.0, and 3.0 mg/kg/h IV; n=6 per group) is compared to iNO (40 ppm; n=6) over a 6 hour period of observation. Hemodynamic parameters are monitored for response to treatment and post-treatment rebound pulmonary arterial hypertension. The activity of R-107 is related to its plasma concentration, in order to construct a pharmacodynamic profile.

Similar studies may be conducted with compounds of the general formula I other than R-107.

Example 9. R-107 is Effective in a Minipig Model of Peripheral Hypertension

In order to test the efficacy of R-107 in peripheral hypertension (HTN), a series of 3 hemodynamic studies is carried out in conscious, instrumented, ambulatory, and telemetered minipigs (n=5) with HTN secondary to an endovascular-created, unilateral, renovascular stenosis. Minipigs are treated with R-107 administered as an enterically-coated oral capsule.

In Series A, the pharmacokinetic profile and hemodynamic effect of a single administration of R-107 (3, 10, 20, 30 mg/kg) is correlated with a one-week washout period between successive dose levels. Animals are monitored for 24 hours to collect continuous hemodynamic data and intermittent plasma concentrations of R-107 and its metabolites (0, 0.25, 0.5, 0.75, 1, 2, 4, 6, 8, 12, 16, 20, and 24 hours). In Series B, the most promising 2 doses of R-107 from Series A are evaluated by carrying out a repeat-dose study of R-107 administered every 6 hours (q6h) for a period of 3 days. The hemodynamic effects of R-107 are correlated with plasma peak and trough concentrations of R-107 and its metabolites obtained q6h. In Series C, the emergence of tachyphylaxis to R-107 in a 2 week repeat-dose study (q6h) is evaluated utilizing the optimal dose determined in Series B, wherein hemodynamics are correlated with plasma pharmacokinetic determinations as in Series B.

Similar studies may be conducted with compounds of the general formula I other than R-107.

Example 10. R-107 is Effective in a Rat Model of Renal Ischemia-Reperfusion Injury In this study, the effect of R-107 at the dose of 80 mg/kg is tested in a well characterized model of kidney ischemia and reperfusion in rats. Male Sprague-Dawley rats are placed onto a thermostatically-controlled heating mat, and body temperature is maintained at 38±10° C. by means of a rectal probe attached to a homeothermic blanket. A tracheotomy is performed to maintain airway patency and to facilitate spontaneous respiration. A midline laparotomy is performed, and the bladder is cannulated. Both kidneys are located, and the renal pedicles, containing the artery, vein, and nerve supplying each kidney, are carefully isolated.

Rats (Groups 2 and 3) are allowed to stabilize for 30 minutes before they are subjected to bilateral renal occlusion for 30 minutes using artery clips to clamp the renal pedicles. Reperfusion commenced once the artery clips are removed (control animals). Occlusion is verified visually by change in the color of the kidneys to a paler shade and reperfusion by a blush. The other rats (Group 1), which underwent identical surgical procedures similar to control animals but did not undergo bilateral renal clamping, are subjected to sham operation (sham operated) and are maintained under anesthesia for the duration of the experiment. At the end of all experiments, animals are killed by an overdose of sodium thiopentone.

Upon completion of surgical procedures, the animals are randomly allocated to Group 1: Sham (no ischemia); Group 2: (ischemia-reperfusion, I/R); and Group 3: (ischemia-reperfusion, I/R, and R-107 therapy). Urine is collected from the rats during the following periods: (i) 2 hours prior to ischemia until 30 minutes prior to ischemia; (ii) from the onset of reperfusion until 1.5 hours after the onset of reperfusion; (iii) from 1.5 hours after the onset of reperfusion until 3.0 hours after the onset of reperfusion; (iv) from 3 hours after the onset of reperfusion until 4.5 hours after the onset of reperfusion; and (v) from 4.5 hours after the onset of reperfusion until 6.0 hours after the onset of reperfusion. Arterial blood samples are obtained at 0, 1.5 hours, 3.0 hours, 4.5 hours, and 6.0 hours after the onset of reperfusion. R-107 (80 mg/kg; Group 3) is administered as a 10 minute IV infusion beginning 20 minutes after the onset of ischemia.

At the end of the reperfusion period, blood (1 ml) samples are collected via the carotid artery into S1/3 tubes containing serum gel, and the samples are centrifuged (6000 rpm for 3 minutes) to separate plasma. All plasma samples are analyzed for biochemical parameters within 24 hours after collection. Urine samples are collected during the reperfusion period, and the volume of urine produced is recorded. Urine concentrations of $Na^+$ are measured and are used in conjunction with plasma $Na^+$ concentrations to calculate fractional excretion of sodium ($FE_{Na}$) using standard formulae, which is used as an indicator of tubular function. Plasma and urine concentrations of creatinine are measured as indicators of impaired glomerular function. Creatinine clearance is calculated using the formula UV/P, where U refers to creatinine concentration in urine, V refers to urine volume/min and P refers to serum creatinine. Plasma concentrations of neutrophil gelatinase-associated lipocalin (NGAL) are evaluated as indicated by the commercial kit. Urine concentration of NGAL is evaluated as indicated by the commercial kit.

Myeloperoxidase (MPO) activity in kidneys is used as an indicator of polymorphonuclear (PMN) cell infiltration using a method previously described. Briefly, at the end of the experiments, kidney tissue is weighed and homogenized in a solution containing 0.5% (wt/vol) hexadecyltrimethyl ammonium bromide dissolved in 10 mmol/l potassium phosphate buffer (pH 7.4) and centrifuged for 30 minutes at 20,000 g at 4° C. An aliquot of supernatant is then removed and added to a reaction mixture containing 1.6 mmol/l tetramethylbenzidine and 0.1 mmol/l hydrogen peroxide ($H_2O_2$). The rate of change in absorbance is measured spectrophotometrically at 650 nm. MPO activity is defined as the quantity of enzyme required to degrade 1 mmol of $H_2O_2$ at 37° C. and is expressed in U/g wet tissue.

Levels of malondialdehyde (MDA) in kidneys are determined as an indicator of lipid peroxidation following a protocol described previously. Briefly, kidney tissue is weighed and homogenized in a 1.15% (wt/vol) KCl solution. A 100 ml aliquot of homogenate is then removed and added to a reaction mixture containing 200 ml 8.1% (wt/vol) lauryl sulfate, 1.5 ml 20% (vol/vol) acetic acid (pH 3.5), 1.5 ml 0.8% (wt/vol) thiobarbituric acid, and 700 ml distilled water. Samples are then boiled for one hour at 95° C. and centrifuged at 3000×g for 10 minutes. The absorbance of the supernatant is measured spectrophotometrically at 650 nm. MDA levels are expressed as μM/100 mg wet tissue.

At post-mortem, a 5 μm section of kidney is removed and placed in formalin and processed through to wax. Five millimeter sections are cut and stained with hematoxylin and eosin. Histologic assessment of tubular necrosis is determined semiquantitatively using a method modified from McWhinnie et al., *Tissue Antigens,* 1987, 29(4), 214-223. Random cortical fields are observed using a ×20 objective. A graticule grid (25 squares) is used to determine the number of line intersects involving tubular profiles. One hundred intersections are examined for each kidney, and a score from 0 to 3 is given for each tubular profile involving an intersection: 0=normal histology; 1=tubular cell swelling, brush border loss, nuclear condensation, with up to one third of tubular profile showing nuclear loss; 2=same as for score 1, but greater than one third and less than two thirds of tubular profile shows nuclear loss; 3=greater than two thirds of tubular profile shows nuclear loss. The total score for each kidney is calculated by addition of all 100 scores.

Similar studies may be conducted with compounds of the general formula I other than R-107.

Example 11. R-107 is Effective in a Murine Model of Retinal Ischemia-Reperfusion Injury In this study, the efficacy of R-107 in subacute murine model of retinal ischemia-reperfusion injury is tested, using male C57BL/6 mice (n=10 per group). Briefly, the anterior chamber of the right eye is cannulated with a 30 gauge needle attached to a line infusing sterile saline. The intraocular pressure (IOP) is raised to 110 mmHg by elevating the saline reservoir. The left eye undergoes sham surgery, in which the needle is inserted into the anterior chamber without elevating IOP. R-107 is injected (30 mg/kg/day IP BID) commencing directly before reperfusion. 2 vehicle controls (normal saline and HPCD) is compared to drug therapy. Treatments are repeated twice daily thereafter until sacrifice. The outcome of these pharmacologic studies is quantitatively assessed by using terminal deoxynucleotidyl transferase dUTP nick end labeling (TUNEL) to measure retinal cell death (after 3 days), confocal imaging to quantify survival of ganglion cell layer neurons (after 7 days), and electroretinogram recordings to measure retinal neuronal function (after 21 days).

Similar studies may be conducted with compounds of the general formula I other than R-107.

Example 12. R-107 is Effective in a Porcine Model of Acute Retinal Ischemia-Reperfusion Injury In this study, a porcine model of acute retinal ischemia-reperfusion injury (n=6 per group) is induced by equilibration with an elevated saline reservoir to create a static IOP of 90 mmHg for 90 min. Task #1: Microvascular responsiveness: A dose-response of parenteral R-107 (0, 10, 30, 80 mg/kg/day IV BID) is initiated 10 minutes before reperfusion. 1 hour after reperfusion, retinal microvessels are harvested and cannulated for ex vivo analysis of vascular responsiveness to endothelium dependent and independent vasodilators. Task #2: Retinal function and morphology: R-107 is given 10 minutes before reperfusion (at a dose determined by Task #1) and its efficacy judged by electroretinogram (1, 2, 7 days post-reperfusion) and retinal histology, ultrastructure, and drug concentration (Day 7).

Similar studies may be conducted with compounds of the general formula I other than R-107.

Example 13. R-107 is Effective in a Rat Model of Myocardial Ischemia-Reperfusion Injury In order to test the efficacy of R-107 in a myocardial ischemia reperfusion injury, male aged Sprague-Dawley rats are dosed with R-107 (0, 10, 30, 80 mg/kg IV) 10 minutes prior to the end of a 30 minutes period of ischemia produced by occlusion of the left anterior descending (LAD) coronary artery. Cardiac function is monitored by a Millar catheter for the determination of heart rate (HR), systolic and diastolic blood pressure (BP), left ventricular (LV) systolic BP, LV end-diastolic BP (LVEDP), ±dP/dt, pressure-volume (PV) loop, and tau (τ). 3 hours post-ischemia, blood and myocardium are analyzed for morphologic, histochemical, and bioanalytical injury. The area of necrosis, as a % of area at risk (AAR), and the extent of the no-reflow zone are quantified.

Similar studies may be conducted with compounds of the general formula I other than R-107.

Example 14. R-107 is Effective in a Minipig Model of Limb Ischemia-Reperfusion Injury In this study, the efficacy of R-107 in a limb ischemia reperfusion injury (LIRI) is tested. In a large animal model of acute LIRI (n=6 minipigs per group) induced by an endovascular balloon occlusion of the femoral artery for 6 hours, parenteral R-107 (0, 10, 30, 80 mg/kg/day TID) is initiated 10 minutes before reperfusion via direct arterial infusion, followed by an IV infusion thereafter. At 7, 14, and 21 days after reperfusion, limb perfusion (by Doppler flow) is correlated with nerve conduction velocity (NCV, per electromyography, EMG), and muscle strength (by foot pressure on a walking surface) with simultaneous plasma concentrations of R-107.

Similar studies may be conducted with compounds of the general formula I other than R-107.

Example 15. R-107 is Effective in a Rat Model of Contrast-Induced Nephropathy

In order to test the efficacy of R-107 in contrast-induced nephropathy (CIN), a single-blinded study of CIN is carried out in Sprague-Dawley rats (n=10 per group) subjected to dehydration, prostaglandin synthetase inhibition, and an IV challenge of contrast media (CM). A sham injury group is compared to treatment of CM-challenged healthy rats with R-107 (10, 20, 40 mg/kg/day in 5% dextrose, BID IV), N-acetylcysteine (NAC, 100 mg/kg/day in 5% dextrose, BID), or vehicle control (hydroxypropyl cyclodextrin, HPCD) initiated 10 min before CM administration and continued for 48 hours. Rats are evaluated at 48 hours for renal function (blood urea nitrogen to creatinine ratio, BUN: creatinine) and parameters reflecting renal injury, including protein release into the blood (NGAL; kidney injury molecule-1, KIM-1), pro-inflammatory transcription factor expression (cytoplasmic IkBa degradation, nuclear p65 translocation), histologic damage (H&E), mitochondrial swelling (electron microscopy), and nuclear damage and DNA repair (PARP activation and nitrosative stress as noted by poly(ADP-ribose) and 3-nitrotyrosine (3-NT) tissue immunoreactivity).

In order to better model the patient population at greatest risk of CIN, the optimal dose of R-107 is then further evaluated, using the same experimental approach and design as before, but in Sprague-Dawley rats previously rendered diabetic 2 weeks earlier by injection of streptozotocin (STZ; 60 mg/kg IV). A control group of rats with STZ-induced diabetes receive vehicle control. If efficacy of R-107 in the diabetic group is less than in healthy rats, additional groups are evaluated at higher doses of R-107 in order to establish the optimal response in this clinically-relevant model of diabetes and CIN. Finally, we investigate whether further benefit may be obtained in the diabetic setting by combining the administration of R-107 with aggressive volume resuscitation, based on the apparent current clinical consensus that increased hydration ameliorates CIN. Diabetic rats in the elevated hydration group receive 10 ml/kg IV normal saline (NS) boluses coincident with the administration of R-107. A control group receives IV NS alone.

Similar studies may be conducted with compounds of the general formula I other than R-107.

Example 16. R-107 is Effective in a Murine $Cl_2$ Exposure Model

In this study, the effect of R-107 in treatment of CILI is tested. Balb/c mice are exposed in a cylindrical glass chamber that is flushed continuously for 60 minutes at a rate of 2 liters/minute with humidified gas obtained from a calibrated cylinder containing air and 400 ppm $Cl_2$. After the end of the 30 minute exposure, the chamber is opened and mice are removed and immediately placed in cages in room air. Two and six hours after the conclusion of $Cl_2$ exposure, mice are administered intraperitoneal (IP) with various doses of R-107. At 24 hours post-exposure to the $Cl_2$-containing air, a midline incision from the neck to the pubis is created for access to the chest and abdominal cavities. Blood samples are obtained from the inferior vena cava just before sacrifice, the heart-lung block is rapidly excised, and the pulmonary circulation is flushed through the main pulmonary artery with 20 ml of normal saline. The lungs are separated from the mediastinal tissues and are taken for biochemical assays and histological examination (H&E staining). The following morphological criteria are used for scoring: grade 0, normal lung; grade 1, minimal edema or infiltration of alveolar or bronchiolar walls; grade 3, moderate edema and inflammatory cell infiltration without obvious damage to lung architecture; and grade 4, severe inflammatory cell infiltration with obvious damage to lung architecture. Similar studies may be conducted with compounds of the general formula I other than R-107.

Figure 2:
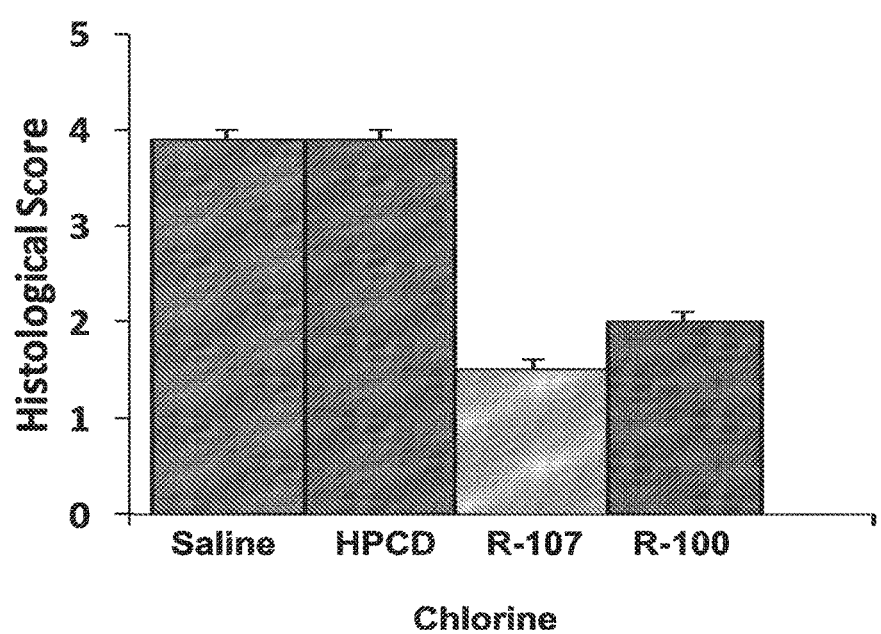
FIG. 2 shows that R-107 (100 mg/kg/dose) as well as its corresponding 1-pyrrolidinyloxy, R-100 (80 mg/kg/dose), when administered 2 and 6 hours post a 60 minute exposure to Cl$_2$ (400 ppm) containing air, significantly attenuated CILI in mice 24 hours post exposure as exemplified by the improved histology scores.

In a particular study, the effect of R-107 in treatment of CILI was tested according to the protocol above. Male Balc/c mice were divided to the following 5 groups: (i) Sham (n=5); (ii) vehicle, HPCD (n=5); (iii) vehicle, PEG-400 (n=5); (iv) R-100 formulated in HPCD, 80 mg/kg/dose, total 160 mg/kg/day, IP (n=10); and (v) R-107 formulated in PEG-400, 100 mg/kg/dose, total 200 mg/kg/day, IP (n=10). FIGS. 1A-1F show representative photomicrographs demonstrating H&E-stained lung sections taken from Sham-operated mice (1A, 1B), animals treated with $Cl_2$+HPCD (1C), animals treated with $Cl_2$+saline (1D), animals treated with $Cl_2$+R-100 (1E), and animals treated with $Cl_2$+R-107 (1F). FIG. 2 shows that R-107 as well as its corresponding 1-pyrrolidinyloxy, R-100, when administered 2 and 6 hours post a 60 minute exposure to $Cl_2$ containing air, significantly attenuated CILI in mice 24 hours post exposure as exemplified by the improved histology scores.

In another study conducted according to the protocol described above, male Balc/c mice were divided to the following 5 groups: (i) Sham (n=2); (ii) vehicle, olive oil (n=4); (iii) R-107 formulated in olive oil, 10 mg/kg/dose, total 20 mg/kg/day, IP (n=4); (iv) R-107 formulated in oil, 30 mg/kg/dose, total 60 mg/kg/day, IP (n=4); and (v) R-107 formulated in oil, 80 mg/kg/dose, total 160 mg/kg/day, IP (n=4). Drug was administered 2 and 6 hours post a 60 minute exposure to $Cl_2$ (400 ppm) containing air, and at 24 hours, the mice were sacrificed and lung histology examined. Table 11 shows that R-107 dose-responsively attenuated CILI in mice 24 hours post exposure as exemplified by the improved histology scores.

TABLE 11

R-107 dose-responsively attenuates CILI in mice 24 hours post exposure as exemplified by the improved histology scores

| N° mice | Histology score | | | | |
|---|---|---|---|---|---|
| | 80 mg/kg | 30 mg/kg | 10 mg/kg | vehicle | Sham |
| 1 | 2.2 | 2.8 | 3.0 | 3.8 | 0 |
| 2 | 1.5 | 2.2 | 3.0 | 4.8 | 0 |
| 3 | 2.0 | 2.4 | 3.5 | 3.4 | |
| 4 | 1.8 | 3.2 | 3.2 | 4.7 | |
| Mean | 1.88 | 2.64 | 3.18 | 4.17 | 0.00 |
| SD | 0.2986 | 0.4488 | 0.2375 | 0.6611 | 0 |
| SE | 0.1493 | 0.2244 | 0.1187 | 0.3306 | 0 |

Example 17. R-107 is Effective in a Rat Model of Erectile Dysfunction

In order to test the efficacy of R-107 in erectile dysfunction (ED), a prospective, placebo-controlled, randomized, single-blinded study of ED is carried out in anesthetized Sprague-Dawley rats (n=10 per group). A sham injury group is compared to treatment with R-107 (80 mg/kg/day BID IV) initiated 10 minutes before crush injury of the cavernosal nerves of the penis and continued for 1 week. After 1 week, rats undergo in vivo neurogenic-mediated evaluation of the erectile response. At the completion of the physiologic evaluation, rats are euthanized and tissues removed for biochemical, morphologic, and inflammatory analyses. The crush injury is produced as follows: After IP injection of sodium pentobarbital (50 mg/kg) for anesthesia, the abdomen is shaved and prepared with an iodine-based solution and a lower midline abdominal incision is made. The prostate gland is exposed and cavernosal nerves tracking posterolateral are identified and isolated. In a sham group there is no further surgical manipulation. In the remaining groups crush injury is created using a hemostat clamp for 3 minutes. The abdomen is then closed in 2 layers in all rats. 1 week after surgical intervention, all rats undergo an in vivo neurogenic-mediated erectile response study. Rats are anesthetized with pentobarbital (50 mg/kg IP) and placed on a thermally regulated surgical table. The trachea is cannulated using PE-240 polyethylene tubing to maintain a patent airway and the animals breath room air enriched with 95% $O_2$/5% $CO_2$. A carotid artery is cannulated with PE-50 tubing to continuously measure systemic blood pressure (MAP) using a Statham transducer attached to a data acquisition system and connected to a computer. A 25 gauge needle filled with heparin (250 U/ml) and connected to PE-50 tubing is inserted into the right crura and connected to a pressure transducer to permit continuous measurement of intracavernous pressure (ICP). The cavernosal nerve (CN) is identified posterolateral to the prostate on 1 side and an electrical stimulator with a stainless steel bipolar hook is placed around the CN. The CN is stimulated with a square pulse stimulator (Grass Instruments, Quincy, Mass.). CN stimulation (CNS) at a frequency of 15 Hz and pulse width of 30 sec is performed in each rat. CNS at 2.5, 5, and 7.5 V is used in the current protocol to achieve significant consistent erectile responses. The duration of stimulation is 1 minute with a rest period of 3-5 minutes between subsequent CNSs. The total erectile response or total ICP is determined by the area under the curve in mm Hg per second from the beginning of CNS until ICP returned to baseline or pre-stimulation pressure. The ICP/MAP ratio at the peak erectile response is determined to control for variations in MAP.

Similar studies may be conducted with compounds of the general formula I other than R-107.

The invention claimed is:

1. A method for reducing oxidative stress or endothelial dysfunction in a mammal in need thereof, said mammal suffering from a wound; diabetic retinopathy; diabetic nephropathy; a hemolytic disease selected from the group consisting of spherocytosis, glucose-6-phosphate dehydrogenase deficiency, sickle cell disease, thalassemia, and paroxysmal nocturnal hemoglobinuria; a cardiovascular disease selected from the group consisting of ischemic heart disease, angina pectoris, myocardial ischemia reperfusion injury and infarction, acute and chronic limb ischemia reperfusion injury, congestive heart failure, atherosclerosis, peripheral arterial hypertension cardiac arrhythmias, idiopathic pulmonary hypertension, pulmonary hypertension associated with idiopathic pulmonary fibrosis, pulmonary hypertension associated with hemolytic disease, primary pulmonary hypertension of the newborn, and pulmonary hypertension secondary to congenital diaphragmatic hernia and meconium aspiration; a neurodegenerative or neurological disorder selected from the group consisting of Alzheimer's disease, Parkinson's disease, amyotrophic lateral sclerosis, multiple sclerosis, convulsive (seizure) disorders, acquired immune deficiency syndrome-dementia and a disorder which involves learning and memory processes; or vaginal dryness, said method comprising administering to said mammal an effective amount of a compound of formula I:

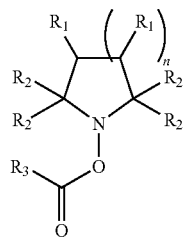

I or an enantiomer, diastereomer, racemate, or a pharmaceutically acceptable salt thereof, wherein each $R_1$ is independently selected from the group consisting of H, —OH, —$COR_4$, —$COOR_4$, —$OCOOR_4$, —$OCON(R_4)_2$, —$(C_1\text{-}C_{16})$alkylene-$COOR_4$, —CN, —$NO_2$, —SH, —$SR_4$, —$(C_1\text{-}C_{16})$alkyl, —O—$(C_1\text{-}C_{16})$alkyl, —$N(R_4)_2$, —$CON(R_4)_2$, —$SO_2R_4$, —$SO_2NHR_4$, —$S(=O)R_4$, and a nitric oxide donor group of the formula —$X_1$—$X_2$—$X_3$, wherein $X_1$ is absent or selected from the group consisting of —O—, —S— and —NH—; $X_2$ is absent or is $(C_1\text{-}C_{20})$alkylene optionally substituted by one or more —$ONO_2$ groups;

and $X_3$ is —NO or —$ONO_2$, provided that at least one $R_1$ group is a nitric oxide donor group;

each $R_2$ is independently selected from the group consisting of $(C_1\text{-}C_{16})$alkyl, $(C_2\text{-}C_{16})$alkenyl, and $(C_2\text{-}C_{16})$alkynyl;

$R_3$ is selected from the group consisting of $(C_1\text{-}C_{10})$alkyl, $(C_3\text{-}C_{10})$cycloalkyl, $(C_6\text{-}C_{14})$aryl, and 4-12-membered heterocyclyl, each of which may optionally be substituted with —OH, —$COR_5$, —$COOR_5$, —$(C_1\text{-}C_8)$alkylene-$COOR_5$, —CN, —$NO_2$, —$(C_1\text{-}C_8)$alkyl, —O—$(C_1\text{-}C_8)$alkyl, —$N(R_5)_2$, —$CON(R_5)_2$, —$SO_2R_5$, —$SO_2NHR_5$, or —$S(=O)R_5$;

each $R_4$ is independently selected from the group consisting of H, $(C_1\text{-}C_8)$alkyl, $(C_3\text{-}C_{10})$cycloalkyl, $(C_6\text{-}C_{14})$aryl, and 4-12-membered heterocyclyl, each of which other than H may optionally be substituted with —OH, —$COR_5$, —$COOR_5$, —$OCOOR_5$, —$OCON(R_5)_2$, —$(C_1\text{-}C_8)$alkylene-$COOR_5$, —CN, —$NO_2$, —SH, —$SR_5$, —$(C_1\text{-}C_8)$alkyl, —O—$(C_1\text{-}C_8)$alkyl, —$N(R_5)_2$, —$CON(R_5)_2$, —$SO_2R_5$, —$SO_2NHR_5$, or —$S(=O)R_5$;

each $R_5$ is independently selected from the group consisting of H, $(C_1\text{-}C_8)$alkyl, $(C_3\text{-}C_{10})$cycloalkyl, $(C_6\text{-}C_{14})$aryl, and 4-12-membered heterocyclyl; and n is 1, 2 or 3.

2. The method of claim 1, wherein each $R_1$ is independently H, —$COOR_4$, —$CON(R_4)_2$, or a nitric oxide donor group of the formula —$X_1$—$X_2$—$X_3$; and $R_4$ is H.

3. The method of claim 1, wherein each $R_2$ is independently $(C_1\text{-}C_8)$alkyl.

4. The method of claim 3, wherein each $R_2$ is identical.

5. The method of claim 1, wherein $R_3$ is $(C_1\text{-}C_8)$alkyl, $(C_1\text{-}C_8)$alkylene-OH, $(C_1\text{-}C_8)$alkylene-$N(R_5)_2$, or $(C_1\text{-}C_8)$alkylene-$COOR_5$, wherein each $R_5$ is independently H, or $(C_1\text{-}C_8)$alkyl.

6. The method of claim 1, wherein $X_1$ is absent or —O—.

7. The method of claim 1, wherein:

each $R_1$ is independently H, —$COOR_4$, —$CON(R_4)_2$, or a nitric oxide donor group of the formula —$X_1$—$X_2$—$X_3$;

each $R_2$ is independently $(C_1\text{-}C_8)$alkyl; $R_3$ is $(C_1\text{-}C_8)$alkyl, $(C_1\text{-}C_8)$alkylene-OH, $(C_1\text{-}C_8)$alkylene-$N(R_5)_2$, or $(C_1\text{-}C_8)$alkylene-$COOR_5$;

each $R_4$ is independently H;

each $R_5$ is independently H or $(C_1\text{-}C_8)$alkyl; and $X_1$ is absent or —O—.

8. The method of claim 1, wherein:

(i) n is 1; and one or two of the carbon atoms at positions 3 or 4 of the pyrrolidine ring are linked to a nitric oxide donor group of the formula —$X_1$—$X_2$—$X_3$;

(ii) n is 2; and one or more of the carbon atoms at positions 3, 4 or 5 of the piperidine ring are linked to a nitric oxide donor group of the formula —$X_1$—$X_2$—$X_3$; or (iii) n is 3; and one or more of the carbon atoms at positions 3, 4, 5 or 6 of the azepane ring are linked to a nitric oxide donor group of the formula —$X_1$—$X_2$—$X_3$.

9. The method of claim 8, wherein said compound has two, three or four identical or different nitric oxide donor groups of the formula —$X_1$—$X_2$—$X_3$.

10. The method of claim 8, wherein each nitric oxide donor group of the formula —$X_1$—$X_2$—$X_3$ is independently —$ONO_2$, —$(C_1\text{-}C_6)$alkylene-$ONO_2$, or —O—$(C_1\text{-}C_6)$alkylene-$ONO_2$, wherein said alkylene is optionally substituted by one or more —$ONO_2$ groups.

11. The method of claim 10, wherein n is 1; each $R_2$ is independently methyl; $R_3$ is methyl, ethyl, or isopropyl; and (i) $R_1$ linked to the carbon atom at position 3 of the pyrrolidine ring is —$CH_2$—$ONO_2$; and $R_1$ linked to the carbon atom at position 4 of the pyrrolidine ring is H;

(ii) $R_1$ linked to the carbon atom at position 3 of the pyrrolidine ring is —$ONO_2$; and $R_1$ linked to the carbon atom at position 4 of the pyrrolidine ring is H;

(iii) each $R_1$ linked to the carbon atoms at positions 3 and 4 of the pyrrolidine ring is independently —$CH_2$—$ONO_2$; or (iv) each $R_1$ linked to the carbon atoms at positions 3 and 4 of the pyrrolidine ring is independently —$ONO_2$.

12. The method of claim 11, wherein said compound is selected from the group consisting of:

2,2,5,5-tetramethyl-3-(nitrooxymethyl)pyrrolidin-1-yl acetate;

2,2,5,5-tetramethyl-3-(nitrooxymethyl)pyrrolidin-1-yl propionate; and 2,2,5,5-tetramethyl-3-(nitrooxymethyl)pyrrolidin-1-yl isobutyrate, or an enantiomer, diastereomer, racemate, or a pharmaceutically acceptable salt thereof.

13. The method of claim 10, wherein n is 2; each $R_2$ is independently methyl; $R_3$ is methyl, ethyl, or isopropyl; and (i) $R_1$ linked to the carbon atom at position 3 of the piperidine ring is —$CH_2$—$ONO_2$; and each $R_1$ linked to the carbon atoms at positions 4 and 5 of the piperidine ring is independently H;

(ii) $R_1$ linked to the carbon atom at position 3 of the piperidine ring is —$ONO_2$; and each $R_1$ linked to the carbon atoms at positions 4 and 5 of the piperidine ring is independently H;

(iii) $R_1$ linked to the carbon atom at position 4 of the piperidine ring is —$CH_2$—$ONO_2$; and each $R_1$ linked to the carbon atoms at positions 3 and 5 of the piperidine ring is independently H;

(iv) $R_1$ linked to the carbon atom at position 4 of the piperidine ring is —$ONO_2$; and each $R_1$ linked to the carbon atoms at positions 3 and 5 of the piperidine ring is independently H;

(v) each $R_1$ linked to the carbon atoms at positions 3 and 4 of the piperidine ring is independently —$CH_2$—$ONO_2$; and $R_1$ linked to the carbon atom at position 5 of the piperidine ring is H;

(vi) each $R_1$ linked to the carbon atoms at positions 3 and 4 of the piperidine ring is independently —$ONO_2$; and $R_1$ linked to the carbon atom at position 5 of the piperidine ring is H;

(vii) each $R_1$ linked to the carbon atoms at positions 3 and 5 of the piperidine ring is independently —$CH_2$—$ONO_2$; and $R_1$ linked to the carbon atom at position 4 of the piperidine ring is H;

(viii) each $R_1$ linked to the carbon atoms at positions 3 and 5 of the piperidine ring is independently —$ONO_2$; and $R_1$ linked to the carbon atom at position 4 of the piperidine ring is H;

(ix) each $R_1$ linked to the carbon atoms at positions 3, 4 and 5 of the piperidine ring is independently —$CH_2$—$ONO_2$; or (x) each $R_1$ linked to the carbon atoms at positions 3, 4 and 5 of the piperidine ring is independently —$ONO_2$.

14. The method of claim 10, wherein n is 3; each $R_2$ is independently methyl; $R_3$ is methyl, ethyl, or isopropyl; and (i) $R_1$ linked to the carbon atom at position 3 of the azepane ring is —$CH_2$—$ONO_2$; and each $R_1$ linked to the carbon atoms at positions 4, 5 and 6 of the azepane ring is independently H;

(ii) $R_1$ linked to the carbon atom at position 3 of the azepane ring is —$ONO_2$; and each $R_1$ linked to the carbon atoms at positions 4, 5 and 6 of the azepane ring is independently H;

(iii) $R_1$ linked to the carbon atom at position 4 of the azepane ring is —$CH_2$—$ONO_2$; and each $R_1$ linked to the carbon atoms at position 3, 5 and 6 of the azepane ring is independently H;

(iv) $R_1$ linked to the carbon atom at position 4 of the azepane ring is —$ONO_2$; and each $R_1$ linked to the carbon atoms at position 3, 5 and 6 of the azepane ring is independently H;

(v) each $R_1$ linked to the carbon atoms at positions 3 and 4 of the azepane ring is independently —$CH_2$—$ONO_2$; and each $R_1$ linked to the carbon atoms at positions 5 and 6 of the azepane ring is independently H;

(vi) each $R_1$ linked to the carbon atoms at positions 3 and 4 of the azepane ring is independently —$ONO_2$; and each $R_1$ linked to the carbon atoms at positions 5 and 6 of the azepane ring is independently H;

(vii) each $R_1$ linked to the carbon atoms at positions 3 and 5 of the azepane ring is independently —$CH_2$—$ONO_2$; and each $R_1$ linked to the carbon atoms at positions 4 and 6 of the azepane ring is independently H;

(viii) each $R_1$ linked to the carbon atoms at positions 3 and 5 of the azepane ring is independently —$ONO_2$; and each $R_1$ linked to the carbon atoms at positions 4 and 6 of the azepane ring is independently H;

(ix) each $R_1$ linked to the carbon atoms at positions 3 and 6 of the azepane ring is independently —$CH_2$—$ONO_2$; and each $R_1$ linked to the carbon atoms at positions 4 and 5 of the azepane ring is independently H;

(x) each $R_1$ linked to the carbon atoms at positions 3 and 6 of the azepane ring is independently —$ONO_2$; and each $R_1$ linked to the carbon atoms at positions 4 and 5 of the azepane ring is independently H;

(xi) each $R_1$ linked to the carbon atoms at positions 3, 4 and 5 of the azepane ring is independently —$CH_2$—$ONO_2$; and $R_1$ linked to the carbon atom at position 6 of the azepane ring is H;

(xii) each $R_1$ linked to the carbon atoms at positions 3, 4 and 5 of the azepane ring is independently —$ONO_2$; and $R_1$ linked to the carbon atom at position 6 of the azepane ring is H;

(xiii) each $R_1$ linked to the carbon atoms at positions 3, 4 and 6 of the azepane ring is independently —$CH_2$—$ONO_2$; and $R_1$ linked to the carbon atom at position 5 of the azepane ring is H;

(xiv) each $R_1$ linked to the carbon atoms at positions 3, 4 and 6 of the azepane ring is independently —$ONO_2$; and $R_1$ linked to the carbon atom at position 5 of the azepane ring is H;

(xv) each $R_1$ linked to the carbon atoms at positions 3, 4, 5 and 6 of the azepane ring is independently —$CH_2$—$ONO_2$; or (xvi) each $R_1$ linked to the carbon atoms at positions 3, 4, 5 and 6 of the azepane ring is independently —$ONO_2$.

15. The method of claim 10, wherein n is 1; each $R_2$ is independently methyl; $R_3$ is methyl, ethyl, or isopropyl; and (i) $R_1$ linked to the carbon atom at position 3 of the pyrrolidine ring is —$CH_2$—$ONO_2$; and $R_1$ linked to the carbon atom at position 4 of the pyrrolidine ring is —$CONH_2$; or (ii) $R_1$ linked to the carbon atom at position 3 of the pyrrolidine ring is —$ONO_2$; and $R_1$ linked to the carbon atom at position 4 of the pyrrolidine ring is —$CONH_2$.

16. The method of claim 10, wherein n is 2; each $R_2$ is independently methyl; $R_3$ is methyl, ethyl, or isopropyl; and
- (i) $R_1$ linked to the carbon atom at position 3 of the piperidine ring is —$CH_2$—$ONO_2$; $R_1$ linked to the carbon atom at position 4 of the piperidine ring is —COOH; and $R_1$ linked to the carbon atoms at position 5 of the piperidine ring is H; or
- (ii) $R_1$ linked to the carbon atom at position 3 of the piperidine ring is —$ONO_2$; $R_1$ linked to the carbon atom at position 4 of the piperidine ring is —COOH; and $R_1$ linked to the carbon atoms at position 5 of the piperidine ring is H.

17. The method of claim 10, wherein:

n is 2;

each $R_2$ is independently methyl;

$R_3$ is methyl, ethyl, or isopropyl;

$R_1$ linked to the carbon atom at position 3 of the piperidine ring is H;

$R_1$ linked to the carbon atom at position 4 of the piperidine ring is —O—$CH_2$—$CH(ONO_2)CH_2$—$ONO_2$; and $R_1$ linked to the carbon atoms at position 5 of the piperidine ring is H.

18. The method of claim 1, wherein said mammal suffers from a wound.

19. The method of claim 18, wherein said mammal suffers from a diabetic wound.

20. The method of claim 1, wherein said mammal is a human.

* * * * *